US009638552B2

United States Patent
Kshirsagar et al.

(10) Patent No.: US 9,638,552 B2
(45) Date of Patent: May 2, 2017

(54) GAS SENSOR HOUSING WITH MICRO-RESONATORS

(71) Applicants: Abhijeet Vikram Kshirsagar, Pune (IN); Chinmaya Rajiv Dandekar, Pune (IN); Amit Barjatya, Barnagar (IN); Shalini Tripathy, Doranda (IN)

(72) Inventors: Abhijeet Vikram Kshirsagar, Pune (IN); Chinmaya Rajiv Dandekar, Pune (IN); Amit Barjatya, Barnagar (IN); Shalini Tripathy, Doranda (IN)

(73) Assignee: Cooper Technologies Company, Houston, TX (US)

( * ) Notice: Subject to any disclaimer, the term of this patent is extended or adjusted under 35 U.S.C. 154(b) by 83 days.

(21) Appl. No.: 14/821,564

(22) Filed: Aug. 7, 2015

(65) Prior Publication Data

US 2017/0038230 A1    Feb. 9, 2017

(51) Int. Cl.
    *G01D 11/24*    (2006.01)
(52) U.S. Cl.
    CPC ................... *G01D 11/245* (2013.01)
(58) Field of Classification Search
    CPC ... G01N 2021/1702; G01N 2021/1704; G01N 2021/3504; G01D 11/24
    USPC ............................................. 73/24.01, 24.02
    See application file for complete search history.

(56) References Cited

U.S. PATENT DOCUMENTS

| 8,117,897 B2* | 2/2012 | Schropp, Jr. ....... G01N 21/1702 250/343 |
| 2005/0035278 A1 | 2/2005 | Margalit et al. |
| 2016/0061784 A1* | 3/2016 | Madhav ............... G01N 29/022 73/24.02 |

FOREIGN PATENT DOCUMENTS

| CN | 102954948 | 6/2013 |
| WO | 2006071171 | 7/2006 |

OTHER PUBLICATIONS

N. Listvina, International Search Report and Written Opinion issued in PCT/US2016/045198 completion date Oct. 27, 2016, mailing date Nov. 10, 2016, 7 pages, Federal Institute of Industrial Property, Moscow, Russia.
Machine translation of CN102954948 via LexisNexis Total Patent, 6 pages.

* cited by examiner

*Primary Examiner* — Lisa Caputo
*Assistant Examiner* — Jamel Williams
(74) *Attorney, Agent, or Firm* — King & Spalding LLP

(57) ABSTRACT

A module for a gas sensor module is described herein. The module can include a first portion. The first portion of the module can include a first body and at least one first micro-resonator coupling feature disposed in and traversing the first body. The first body can be configured to be disposed within a cavity of a housing of the gas sensor. The at least one first micro-resonator coupling feature can be configured to align with at least one optical device of the gas sensor when the first body is disposed within the cavity of housing of the gas sensor. The at least one first micro-resonator coupling feature can be configured to have at least one first micro-resonator disposed therein.

20 Claims, 12 Drawing Sheets

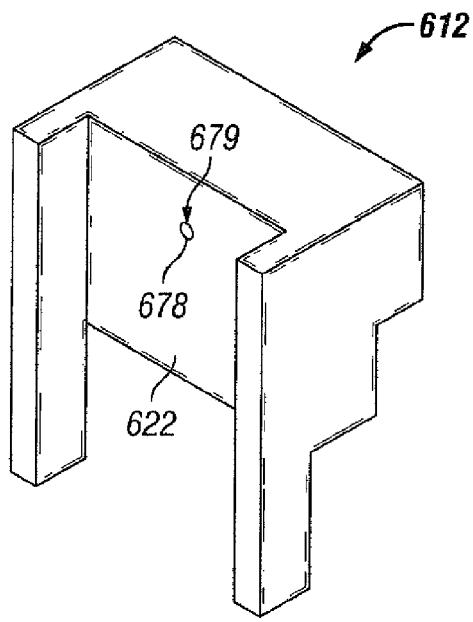 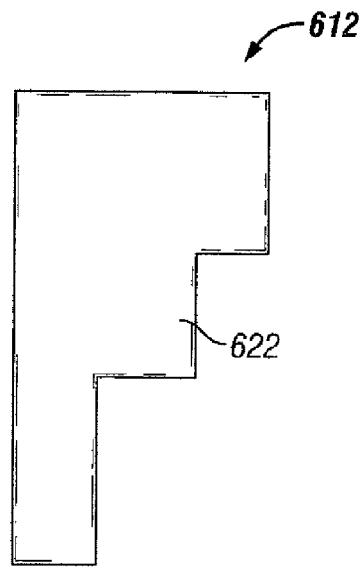
FIG. 6A                FIG. 6B
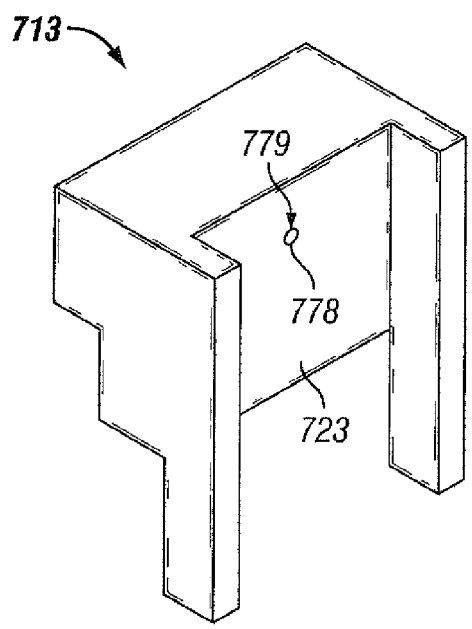 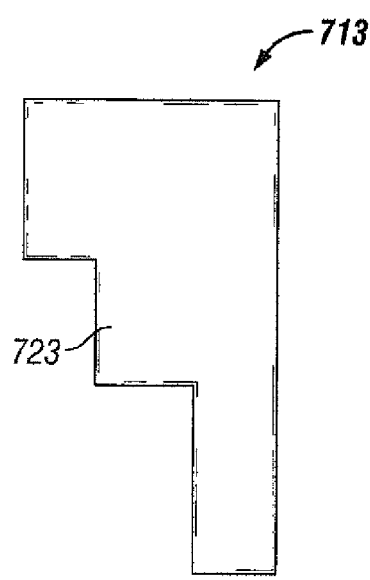
FIG. 7A                FIG. 7B

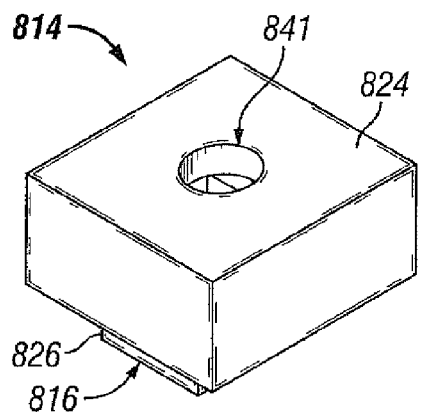
FIG. 8A
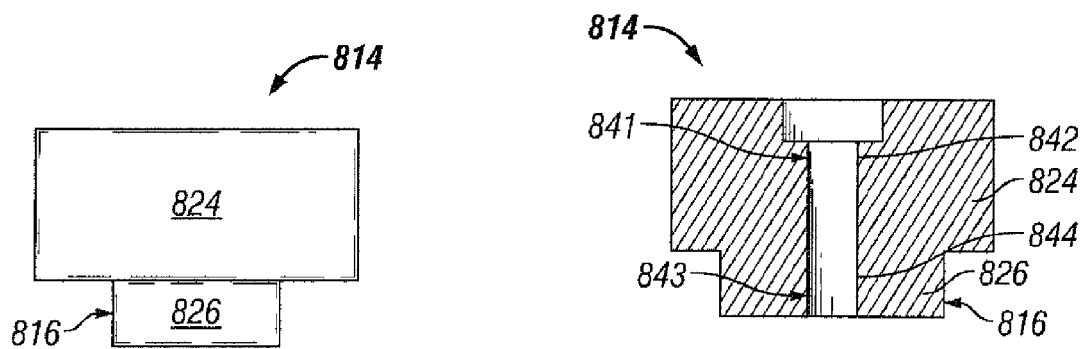
FIG. 8B
FIG. 8C
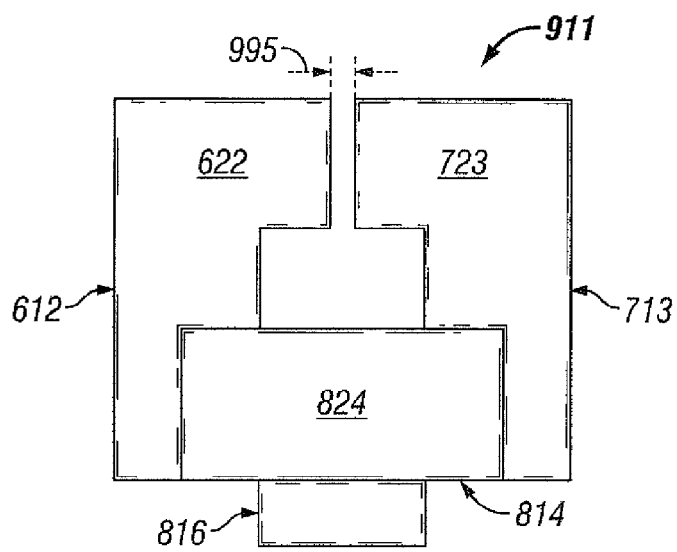
FIG. 9

GAS SENSOR HOUSING WITH MICRO-RESONATORS

TECHNICAL FIELD

Embodiments described herein relate generally to gas sensors, and more particularly to systems, methods, and devices for housings with micro-resonators for optical gas sensors.

BACKGROUND

The detection and measurement of trace gas concentrations is important for both the understanding and monitoring of a wide variety of applications, such as environmental monitoring, industrial process control analysis, combustion processes, detection of toxic and flammable gases, as well as explosives. For example, trace gas sensors capable of high sensitivity and selectivity can be used in atmospheric science for the detecting and monitoring of different trace gas species including greenhouse gases and ozone, and in breath diagnostics, for detection and monitoring of nitric oxide, ethane, ammonia and numerous other biomarkers. As another example, in gas-to-grid applications, methane generated from a biogas process is tested for impurities (e.g., hydrogen sulfide or $H_2S$) to determine whether the methane is pure enough to be mixed directly with natural gas.

SUMMARY

In general, in one aspect, the disclosure relates to a module for a gas sensor. The gas sensor can include a first portion having a first body and at least one first micro-resonator coupling feature disposed in and traversing the first body. The first body can be configured to be disposed within a cavity of a housing of the gas sensor. The at least one first micro-resonator coupling feature can be configured to align with at least one optical device of the gas sensor when the first body is disposed within the cavity of the housing of the gas sensor. The at least one first micro-resonator coupling feature can be configured to have at least one first micro-resonator disposed therein In another aspect, the disclosure can generally relate to a housing for a gas sensor module. The housing can include a first housing portion and a module disposed within the first cavity and coupled to the first housing portion. The first housing portion of the housing can include at least one first wall forming a first cavity. The first housing portion of the housing can also include a first optical device coupling feature disposed at a first location in the at least one first wall, where the first location is adjacent to the first cavity. The first housing portion of the housing can further include a module coupling feature disposed at a second location in the at least one first wall, where the second location is adjacent to the first cavity. The module of the housing can include a first portion and a second portion. The first portion of the module can include a first body and at least one first micro-resonator coupling feature disposed in and traversing the first body. The second portion of the module can also include a second body and a housing coupling feature disposed in the second body, where the housing coupling feature couples to the module coupling feature of the first housing portion. The at least one first micro-resonator coupling feature can be aligned with the first optical device coupling feature of the first housing portion. The first optical device coupling feature can be configured to have a first optical device disposed therein. The at least one first micro-resonator coupling feature can be configured to have at least one first micro-resonator disposed therein.

In yet another aspect, the disclosure can generally relate to a gas sensor. The gas sensor can include a housing. The housing of the gas sensor can include at least one wall forming a cavity, and at least one optical device coupling feature disposed at a first location in the at least one wall, where the first location is adjacent to the cavity. The housing of the gas sensor can also include a first tuning fork coupling feature disposed at a second location in the at least one wall, where the second location is adjacent to the cavity. The gas sensor can also include a module. The module of the gas sensor can include a body, and at least one micro-resonator coupling feature disposed in and traversing the body at a second location of the body. The module of the gas sensor can also include a second tuning fork coupling feature disposed in and traversing the body at a third location of the body, where the second tuning fork coupling feature is substantially perpendicular to the at least one micro-resonator coupling feature. The gas sensor can further include at least one optical device coupled to the at least one optical device coupling feature of the housing, and at least one micro-resonator coupled to the at least one micro-resonator coupling feature of the module. The gas sensor can also include a tuning fork coupled to the first tuning fork coupling feature of the housing and the second tuning fork coupling feature of the module. The at least one micro-resonator and the at least one optical device can be substantially aligned with each other.

These and other aspects, objects, features, and embodiments will be apparent from the following description and the appended claims.

BRIEF DESCRIPTION OF THE DRAWINGS

The drawings illustrate only example embodiments of housings for optical gas sensors and are therefore not to be considered limiting of its scope, as housings for optical gas sensors may admit to other equally effective embodiments. The elements and features shown in the drawings are not necessarily to scale, emphasis instead being placed upon clearly illustrating the principles of the example embodiments. Additionally, certain dimensions or positionings may be exaggerated to help visually convey such principles. In the drawings, reference numerals designate like or corresponding, but not necessarily identical, elements.

FIGS. 6A and 6B show a portion of a module for a gas sensor in accordance with certain example embodiments.

FIGS. 7A and 7B show another portion of a module for a gas sensor in accordance with certain example embodiments.

FIGS. 8A-8C show yet another portion of a module for a gas sensor in accordance with certain example embodiments.

FIG. 9 shows a side view of a module for a gas sensor that includes the portions of FIGS. 6A-8C in accordance with certain example embodiments.

DETAILED DESCRIPTION OF EXAMPLE EMBODIMENTS

Figure 1:
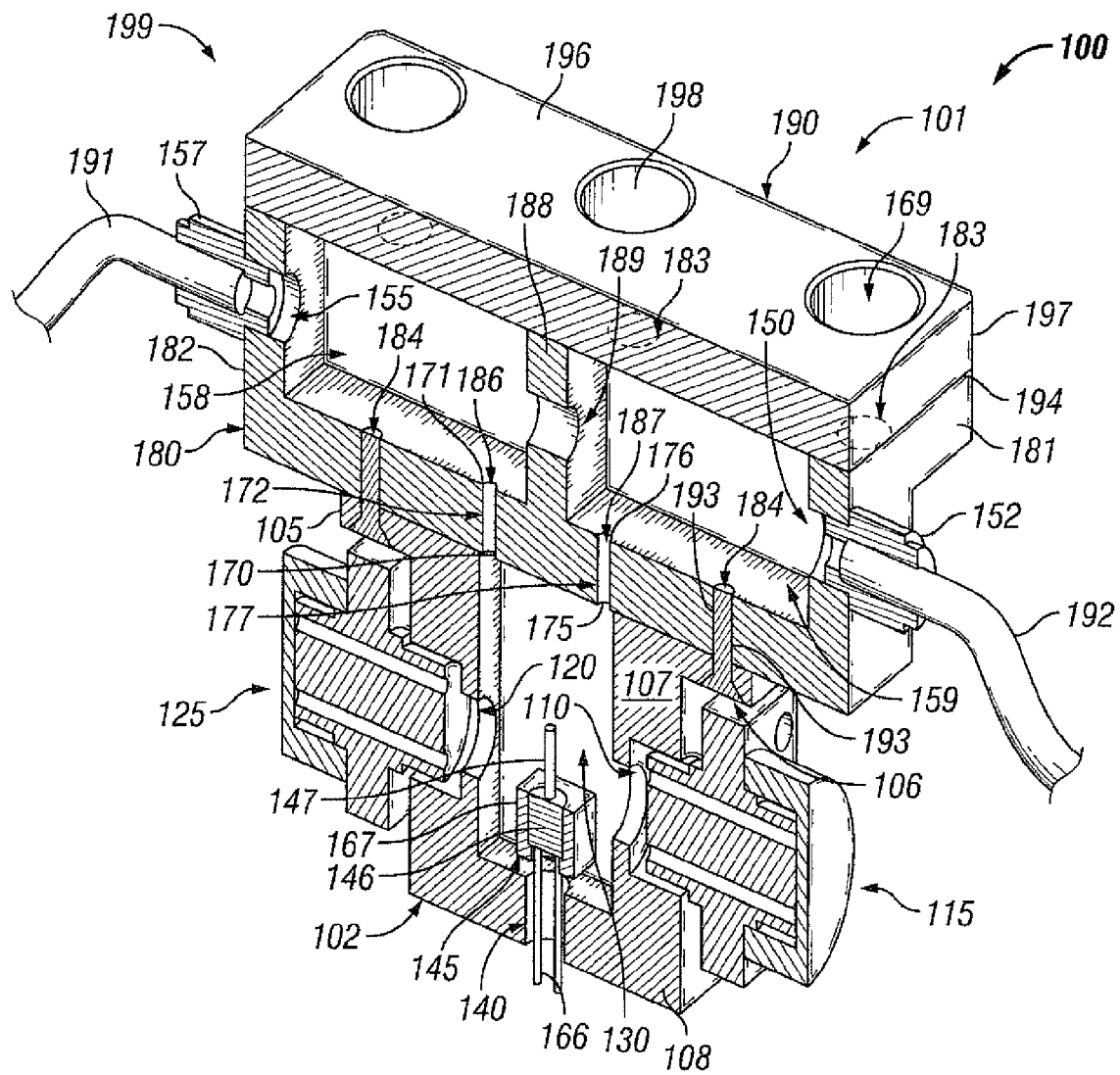
FIG. 1 shows a top-side cross-sectional perspective view of a subassembly of a gas sensor in accordance with certain example embodiments.

The example embodiments discussed herein are directed to systems, apparatuses, and methods related to housings for optical gas sensors that include micro-resonators. Optical gas sensors can have a number of configurations and use a number of technologies. For example, a quartz-enhanced photo-acoustic spectroscopic (QEPAS) sensor can have an optical irradiation at a gas-specific wavelength directed through a gap between the prongs of a quartz tuning fork (QTF) vibrating at its resonating frequency. The optical energy is absorbed and released by the gas, causing a change in the resonant frequency of the QTF. The amount of change in the resonant frequency of the QTF is proportional to the concentration of the gas molecules.

While example embodiments are described herein as being directed to optical gas sensors, example embodiments can also be used with other types of sensors. Further, optical gas sensors that can be used with example embodiments can have any of a number of configurations not shown or described herein. As described herein, a user can be any person that interacts with example optical gas sensors. Examples of a user may include, but are not limited to, a consumer, an operations specialist, a gas engineer, a supervisor, a consultant, a contractor, an operator, and a manufacturer's representative.

In one or more example embodiments, example housings for optical gas sensors are subject to meeting certain standards and/or requirements. For example, the International Electrotechnical Commission (IEC) sets standards, such as IEC 60079-28 that applies to optical gas sensors, with which example housings must comply to be used in field applications. Examples of other entities that set applicable standards and regulations include, but are not limited to, the National Electrical Manufacturers Association (NEMA), the National Electric Code (NEC), the Institute of Electrical and Electronics Engineers (IEEE), and Underwriters Laboratories (UL).

In some cases, the example embodiments discussed herein can be used in any type of hazardous environment, including but not limited to an airplane hangar, a drilling rig (as for oil, gas, or water), a production rig (as for oil or gas), a refinery, a chemical plant, a power plant, a mining operation, a wastewater treatment facility, and a steel mill. The housings for optical gas sensors (or components thereof) described herein can be physically placed in and/or used with corrosive components (e.g., gases). In addition, or in the alternative, example housings for optical gas sensors (or components thereof) can be subject to extreme heat, extreme cold, moisture, humidity, dust, and other conditions that can cause wear on the housings for optical gas sensors or portions thereof In certain example embodiments, the housings for optical gas sensors, including any components and/or portions thereof, are made of one or more materials that are designed to maintain a long-term useful life and to perform when required without mechanical and/or other types of failure. Examples of such materials can include, but are not limited to, aluminum, stainless steel, fiberglass, glass, plastic, ceramic, nickel-based alloys, and rubber. Such materials can be resistant to corrosion, corrosive materials (e.g., $H_2S$ gas) and other harmful effects that can be caused by the test gas, the tested gas, and/or the environment in which the gas sensor housing is exposed.

Any components (e.g., inlet tube coupling feature, receiving channel) of example housings for optical gas sensors, or portions thereof, described herein can be made from a single piece (as from a mold, injection mold, die cast, or extrusion process). In addition, or in the alternative, a component (or portions thereof) can be made from multiple pieces that are mechanically coupled to each other. In such a case, the multiple pieces can be mechanically coupled to each other using one or more of a number of coupling methods, including but not limited to epoxy, welding, fastening devices, compression fittings, mating threads, and slotted fittings. One or more pieces that are mechanically coupled to each other can be coupled to each other in one or more of a number of ways, including but not limited to fixedly, hingedly, removeably, slidably, and threadably.

Components and/or features described herein can include elements that are described as coupling, fastening, securing, abutting, or other similar terms. Such terms are merely meant to distinguish various elements and/or features within a component or device and are not meant to limit the capability or function of that particular element and/or feature. For example, a feature described as a "coupling feature" can couple, secure, fasten, abut, and/or perform other functions aside from, or in addition to, merely coupling.

A coupling feature (including a complementary coupling feature) as described herein can allow one or more components (e.g., a housings) and/or portions of optical gas sensors to become mechanically and/or electrically coupled, directly or indirectly, to another portion of the optical gas sensor. A coupling feature can include, but is not limited to, a clamp, a portion of a hinge, an aperture, a recessed area, a protrusion, a slot, a spring clip, a tab, a detent, a threaded coupling, and mating threads. One portion of an example optical gas sensor can be coupled to another portion of the optical gas sensor by the direct use of one or more coupling features. In addition, or in the alternative, a portion of an example optical gas sensor can be coupled to another portion of the optical gas sensor using one or more independent devices that interact with one or more coupling features disposed on a component of the optical gas sensor. Examples of such devices can include, but are not limited to, a pin, a hinge, a fastening device (e.g., a bolt, a screw, a rivet), and a spring.

One coupling feature described herein can be the same as, or different than, one or more other coupling features described herein. A complementary coupling feature as described herein can be a coupling feature that mechanically couples, directly or indirectly, with another coupling feature. For any figure shown and described herein, one or more of the components may be omitted, added, repeated, and/or substituted. Accordingly, embodiments shown in a particular figure should not be considered limited to the specific arrangements of components shown in such figure.

Further, if a component of a figure is described but not expressly shown or labeled in that figure, the label used for a corresponding component in another figure can be inferred to that component. Conversely, if a component in a figure is labeled but not described, the description for such component can be substantially the same as the description for the corresponding component in another figure. The numbering scheme for the various components in the figures herein is such that each component is represented by a three or four digit number, and the three or four digit number representing corresponding components in other figures have the identical last two digits.

Example embodiments of housings for optical gas sensors will be described more fully hereinafter with reference to the accompanying drawings, in which example housings for optical gas sensors are shown. Housings for optical gas sensors may, however, be embodied in many different forms and should not be construed as limited to the example embodiments set forth herein. Rather, these example embodiments are provided so that this disclosure will be thorough and complete, and will fully convey the scope of housings for optical gas sensors to those of ordinary skill in the art. Like, but not necessarily the same, elements (also sometimes called components) in the various figures are denoted by like reference numerals for consistency.

Terms such as "top", "bottom", "left", "right", "inner," "outer," "end," "distal", "proximal", "first", and "second" are used merely to distinguish one component (or part of a component or state of a component) from another. Such terms are not meant to denote a preference or a particular orientation, and are not meant to limit embodiments of housings for optical gas sensors. In the following detailed description of the example embodiments, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Also, the names given to various components described herein are descriptive of example embodiments and are not meant to be limiting in any way. Those skilled in the art will appreciate that a feature and/or component shown and/or described in one embodiment (e.g., in a figure) herein can be used in another embodiment (e.g., in any other figure) herein, even if not expressly shown and/or described in such other embodiment.

FIG. 1 shows a top-side cross-sectional perspective view of a portion of a subassembly 100 of a gas sensor in accordance with certain example embodiments. The subassembly 100 in this case includes a gas sensor housing 101, an optical device 315 disposed in the optical device coupling feature 110, an optical device 325 disposed in the optical device coupling feature 120, a tuning fork 345 disposed in the tuning fork coupling feature 140, an inlet tube 192 disposed in the inlet tube coupling feature 150, and an outlet tube 191 disposed in the outlet tube coupling feature 155.

Referring to FIG. 1, the gas sensor housing 101 can have a single portion or multiple (e.g., two, three, four) portions. For example, as shown in FIG. 1, the gas sensor housing 101 can include a top portion 199 and a bottom portion 102. In such a case, each portion of the gas sensor housing 101 can have at least one cavity. In this example, the top portion 199 has a cavity (defined by cavity portion 158 and cavity portion 159), and the bottom portion 102 has a cavity 130. The top portion 199 and the bottom portion 102 of the housing 101 can have any of a number of shapes and sizes that are the same or different than each other. For example, the top portion 199 and the bottom portion 102 of the housing 101 shown in FIG. 1 are rectangular parallelepiped in shape, with the top portion 199 being wider than the bottom portion 102.

The gas sensor housing 101 can be configured to perform any measurements of the gas being tested (also called the test gas herein). For this to occur, the various portions (e.g., top portion 199, bottom portion 102) of the example housing 101 can be coupled to each other in such a way that one portion (e.g., top portion 199) delivers the test gas to another portion (e.g., bottom portion 102), and also receives the tested gas (the test gas that has been tested) from the other portion of the housing 101. The example housing 101 (or portion thereof) can include at least one wall that forms a cavity. For example, the top portion 199 of the housing 101 in this case has a top wall 190 (also sometimes called a top plate 190), a side wall 182, and a bottom wall 185 that forms the cavity of the top portion 199. As another example, the bottom portion 102 of the housing 101 in this case has a side wall 107 and a bottom wall 108 that forms the cavity 130.

The cavity of the top portion 199 and the cavity 130 of the bottom portion 102 can be completely enclosed, substantially enclosed, or partially enclosed. For example, if the top plate 190 is removed, the cavity of the top portion 199 would be partially enclosed. As another example, if the bottom portion 102 and the top portion 199 of the housing 101 are detachable, the bottom portion 102 shown in FIGS. 1 and 3 would be partially enclosed because the top wall 105 of the bottom portion 102 cover the cavity 130, and so the cavity 130 is instead enclosed by the bottom wall 185 of the top portion 199 when the top portion 199 and the bottom portion 102 are coupled to each other.

In certain example embodiments, the cavity of the top portion 199 has multiple (e.g., two, three, four) portions. For example, in this case the cavity of the top portion 199 is divided into a first cavity portion 158 and a second cavity portion 159. When the cavity of the top portion 199 (or any other portion of the housing 101) has multiple cavity portions, each cavity portion can be virtually or physically separated from other cavity portions of the cavity of the top portion 199. For example, in this case, the first cavity portion 158 and the second cavity portion 159 are physically separated from each other by a partition 188. In such a case, the partition 188 can have or include one or more of a number of characteristics. Examples of such characteristics can include, but are not limited to, a solid configuration, a porous material, a non-porous material, a mesh, and an orifice (such as orifice 189).

When the cavity portions of the top portion 199 of the housing 101 of FIG. 1 are physically separated from each other by the partition 188, the partition 188 can substantially isolate one cavity portion (e.g., cavity portion 158) from the other cavity portions (e.g., cavity portion 159) of the top portion 199 of the housing 101. A partition 188 can be temporary or permanent with respect to its position in the cavity of the top portion 199. There can be multiple partitions 188. In addition, or in the alternative, a partition 188 can have no orifice or multiple orifices 189. An orifice 189 can traverse some or all of the thickness of a partition 188.

The partition 188 can also help reduce and/or control the flow rate and/or turbulent flow of the test gas, which in turn can control the flow of the test gas sent to another portion (e.g., bottom portion 102) of the housing 101. The partition 188 can also help regulate one or more of a number of parameters (e.g., pressure) within the cavity of the top portion 199. If the cavity of the top portion 199 has multiple cavity portions, the shape and size of one portion of the cavity can be the same as, or different than, the shape and size of the other portions of the cavity. For example, in this case, cavity portion 158 can have substantially the same shape and size as the cavity portion 159.

In certain example embodiments, the top portion 199 is coupled to one or more other portions of the housing 101. For example, in this case, top portion 199 is coupled to the bottom potion 102 of the housing 101. The top portion 199 can be coupled to the bottom portion 102 using one or more of a number of coupling features 184 (sometimes called a bottom portion coupling feature 184). For example, in FIG. 1, the coupling features 184 are two apertures that traverse the thickness of the bottom wall 185 of the top portion 199 and that are disposed substantially equidistantly from the partition 189 that divides the cavity portion 158 from the cavity portion 159.

In this case, one coupling feature 184 is disposed adjacent to cavity portion 158, and the other coupling feature 184 is disposed adjacent to cavity portion 159. When a coupling feature 184 is an aperture, such as in this case, each coupling feature 184 can receive a fastening device 193 (e.g., a bolt, a screw, a rivet) that is used to couple the top portion 199 to the bottom portion 102. A coupling feature 184 can also be disposed, in whole or in part, within another wall (e.g., side wall 182) of the top portion 199.

The characteristics (e.g., shape, size, configuration) of the coupling features 184 can be configured to correspond to the associated characteristics of coupling features (e.g., coupling features 106) of the bottom portion 102, described below. In such a case, the top portion 199 can be coupled to the bottom portion 102 in one or more certain orientations. The top portion 199 can include one or more features to accommodate the coupling features 184. For example, there can be mating threads disposed along the inner surface of the bottom wall 185 that forms the coupling feature 184.

In certain example embodiments, the top portion 199 of the housing 101 includes one or more features that interact with one or more other components of the housing 101 and/or an optical gas sensor. For example, as shown in FIG. 1, the top portion 199 can include an inlet tube coupling feature 150, an outlet tube coupling feature 155, a distribution channel 187, and a receiving channel 186. In such a case, the inlet tube coupling feature 150 can couple to the inlet tube 192 (described below). The inlet tube coupling feature 150 can include one or more of a number of coupling features. For example, in this example, the inlet tube coupling feature 150 can be an aperture that traverses a side wall 182 of the top portion 199. The inlet tube 192 is configured to deliver test gas into the cavity portion 159 of the top portion 199 of the housing 101.

To deliver the test gas from the cavity portion 159 of the top portion 199 to the cavity 130 of the bottom portion 102 of the housing 101, the top portion 199 can include one or more distribution channels 187. In such a case, the distribution channel 187 can include one or more features (e.g., side walls) sufficient to allow test gas to pass therethrough. The distribution channel 187 can be disposed, at least in part, in a wall (e.g., bottom wall 185) of the top portion 199. Further, the distribution channel 187 can be located adjacent to a portion (e.g., cavity portion 159) of the cavity of the top portion 199. In certain example embodiments, the distribution channel 187 is adjacent to the same portion of the cavity as the inlet tube coupling feature 150. For example, in this case, the distribution channel 187 and the inlet tube coupling feature 150 are each located adjacent to cavity portion 159 at different positions along a wall (or, in this case, different walls) of the top portion 199.

In some cases, the distribution channel 187 transports the test gas from the top portion 199 to the bottom portion 102 of the housing 101. For example, in this case, the distribution channel 187 is disposed in the bottom wall 185 of the top portion 199 of the housing 101. In certain example embodiments, the distribution channel 187 (or portions thereof) can include a partition, as with the partition 188 described above with respect to the cavity of the top portion 199, to help control the flow of the test gas as the test gas flows to the cavity 130 of the bottom portion 102.

To continue with the circulation process involving the test gas, once the test gas is tested inside the cavity 130 of the bottom portion 102, the resulting gas (called the tested gas) is removed from the cavity 130 of the bottom portion 102. To receive the tested gas by the top portion 199 from the bottom portion 102, the top portion 199 can include one or more receiving channels 186 that can include one or more features (e.g., side walls) sufficient to allow tested gas to pass therethrough. The receiving channel 186 can be disposed, at least in part, in a wall (e.g., bottom wall 185) of the top portion 199. Further, the receiving channel 186 can be located adjacent to a portion (e.g., cavity portion 158) of the cavity of the top portion 199. In certain example embodiments, the receiving channel 186 is adjacent to the same portion of the cavity as the outlet tube coupling feature 155, described below. For example, in this case, the receiving channel 186 and the outlet tube coupling feature 155 are each located adjacent to cavity portion 158 at different positions along a wall (or, in this case, different walls) of the top portion 199.

In some cases, the receiving channel 186 transports the tested gas from the bottom portion 102 of the housing 101 to the top portion 199. For example, in this case, the receiving channel 186 is disposed in the bottom wall 185 of the top portion 199 of the housing 101. In certain example embodiments, the receiving channel 186 (or portions thereof) can include a partition, as with the partition 188 described above with respect to the cavity of the top portion 199, to help control the flow of the tested gas as the tested gas flows from the cavity 130 of the bottom portion 102 to the cavity portion 158 of the top portion 199.

To complete the circulation process involving the tested gas, the outlet tube coupling feature 155 of the top portion 199 can couple to an outlet tube 191 (described below). The outlet tube coupling feature 155 can include one or more of a number of coupling features. For example, in this example, the outlet tube coupling feature 155 can be an aperture that traverses a side wall 182 of the top portion 199. The outlet tube 191 is configured to remove tested gas from the cavity portion 158 of the top portion 199 of the housing 101.

As discussed above, in certain example embodiments, the top portion 199 of the housing 101 can have one or more channels (e.g., distribution channel 186, receiving channel 187) disposed in the main body 180. Such channels can be used, for example, to inject test gas into and/or remove tested gas from the cavity 130 of the bottom portion 102 of the housing 101. Channel 187 can be disposed in a different location (relative to the location of channel 186) in the main body 180 of the top portion 199 of the housing 101. Each channel can have any of a number of features, shapes, sizes, and/or orientations. For example, in this case, channel 186 can include a channel wall 172 that is disposed in the main body 180 of the top portion 199 and that is substantially linear. The channel 186 in this case also has a first end 171 disposed at the outer surface of the bottom wall 185 and a second end 170 disposed at the inner surface of the bottom wall 185 (adjacent to the cavity portion 159).

Similarly, channel 187 can include a channel wall 177 that is disposed in the main body 180 of the top portion 199 and that is substantially linear. The channel 187 in this case also has a first end 176 disposed at the outer surface of the bottom wall 185 and a second end 175 disposed at the inner surface of the bottom wall 185 (adjacent to the cavity portion 158). In this case, channel 186 is substantially parallel with channel 187. The channel wall of a channel can be coated with one or more of a number of materials. In addition, or in the alternative, the channel wall of a channel can have a sleeve (e.g., a distribution tube, a receiving tube) or some similar component of the gas sensor module disposed therein.

The first end (e.g., first end 171, first end 176) of a channel can also be disposed at an inner surface of a side wall 182 of the main body 180 or at some other location on the top portion 199, depending on one or more of a number of factors, including but not limited to the characteristics (e.g., shape, size, orientation) of the top portion 199, and the location of one or more components (e.g., a gas injector, a gas collector) of the gas sensor module. A channel (e.g., distribution channel 186, receiving channel 187) can be linear, curved, angled, and/or have one or more of any other shapes. Similarly, a channel wall (e.g., channel wall 172, channel wall 177) of a channel can have any of a number of characteristics (e.g., size, cross-sectional shape, length, width) suitable for the gas sensor module.

In certain example embodiments, the top portion 199 of the housing 101 can include multiple components that are mechanically coupled to each other. For example, as shown in FIG. 1, the top plate 190 of the top portion 199 can be a separate component from the main body 180 of the top portion 199. In such a case, the top plate 190 can be coupled to the main body 180 in one or more of a number of ways (e.g., fixedly, removably, hingedly). In this example, the top plate 190 is removably coupled to the main body 180. Specifically, the top plate 190 of FIG. 1 includes a number of coupling features 198 (in this case, apertures) that align with and couple to, directly or indirectly, complementary coupling features 183 (also apertures in this case) disposed in a side extension 181 of the main body 180.

In this example, the coupling features 198 traverse at least a portion of the thickness (between the top surface 196 and the bottom surface 194) of the top plate 190. The thickness of the top plate 190 is substantially the same as the height of the side wall 197 of the top plate 190. Similarly, in this case, the coupling features 183 traverse at least a portion of the thickness of the side extensions 181 of the main body 180. In this case, the coupling features 183 and the coupling features 198 are indirectly coupled to each other by coupling features 169, which in this case are fastening devices (e.g., screws, bolts).

As another example, the top plate 190 and/or the main body 180 of the top portion 199 of the housing 101 can be made of multiple pieces. Similarly, the bottom portion 102 can be made of multiple pieces. For example, the view of the top plate 190 the main body 180, and the bottom portion 102 shown in FIG. 1 can be actual pieces of those components that are coupled to mirror images of those components to form a substantial enclosure of cavity portion 158, cavity portion 159, and cavity 130. When the top portion 199 or the bottom portion 102 is made of multiple pieces, the multiple pieces can be substantially symmetrical to each other. Alternatively, the multiple pieces can have non-symmetrical shapes relative to each other.

In any case, when the various pieces of the top portion 199 and/or the various pieces of the bottom portion 102 abut against each other (couple to each other), the various cavities (or portions thereof) become substantially whole and continuous. Further, when the various pieces are coupled to each other, the associated coupling features (e.g., the inlet tube coupling feature 150, the outlet tube coupling feature 155, the tuning fork coupling feature 140 (described below), the distribution channel 187, the receiving channel 186) can be made whole. In such a case, one or more of these pieces can include additional coupling features to facilitate coupling those pieces to each other.

The bottom portion 102 can have at least one wall that forms the cavity 130. For example, in this case, the bottom portion 102 of the housing 101 includes a bottom wall 108 and a side wall 107. The cavity 130 formed the walls of the bottom portion 102 can have a shape and size sufficient to test the test gas distributed into the cavity 130 based on the other components (e.g., tuning fork, optical device) used to test the test gas. For example, as shown in FIG. 1, the cavity 130 can be substantially rectangular parallelepiped in shape.

In certain example embodiments, the bottom portion 102 of the housing 101 includes one or more features that interact with one or more other components of the housing 101 and/or an optical gas sensor. For example, as shown in FIG. 1, the bottom portion 102 can include a tuning fork coupling feature 140, an optical device coupling feature 110, and an optical device coupling feature 120.

The tuning fork coupling feature 140 (or portion thereof) can couple, directly or indirectly, to a tuning fork 145, described below. The tuning fork coupling feature 140 can have a shape and size to host one or more of a number of tuning forks. The tuning fork coupling feature 140 can be disposed at any location along an inner surface of a wall (e.g., bottom wall 108) that forms the cavity 130. For example, as shown in FIG. 1, the tuning fork coupling feature 140 can be disposed in the approximate center of the inner surface of the bottom wall 108 adjacent to the cavity 130. The tuning fork coupling feature 140 can include any of a number of features (e.g., a collar, a notch, a protrusion, a recess) to help in coupling the tuning fork with the tuning fork coupling feature 140. In addition, the tuning fork coupling feature 140 can be disposed along an inner surface of another wall (e.g., side wall 107) adjacent to the cavity 130.

In certain example embodiments, the optical device coupling feature 120 (or a portion thereof) can couple, directly or indirectly, to an optical device 125, described below. The optical device coupling feature 120 can have a shape and size to host one or more of a number of optical devices. The optical device coupling feature 120 can be disposed at any location along an inner surface of a wall (e.g., side wall 107) that forms the cavity 130. For example, as shown in FIG. 1, the optical device coupling feature 120 can be disposed in the inner surface of the side wall 107 at a particular lateral location relative to the tuning fork coupling feature 140 adjacent to the cavity 130. The optical device coupling feature 120 can include any of a number of features (e.g., a collar, a notch, a protrusion, a recess) to help in coupling an optical device 125 with the optical device coupling feature 120. In addition, the optical device coupling feature 120 can be disposed along an inner surface of another wall (e.g., bottom wall 108) adjacent to the cavity 130.

Similarly, the optical device coupling feature 110 (or a portion thereof) can couple, directly or indirectly, to an optical device 115, described below. The optical device coupling feature 110 can have a shape and size to host one or more of a number of optical devices. The optical device coupling feature 110 can be disposed at any location along an inner surface of a wall (e.g., side wall 107) that forms the cavity 130. For example, as shown in FIG. 1, the optical device coupling feature 110 can be disposed in the inner surface of the side wall 107 at a particular lateral location relative to the tuning fork coupling feature 140 and to the optical device coupling feature 120, adjacent to the cavity 130. The optical device coupling feature 110 can include any of a number of features (e.g., a collar, a notch, a protrusion, a recess) to help in coupling an optical device 115 with the optical device coupling feature 110. In addition, the optical device coupling feature 110 can be disposed along an inner surface of another wall (e.g., bottom wall 108) adjacent to the cavity 130.

In addition to, or in the alternative of, the tuning fork coupling feature 140, the optical device coupling feature 110, and/or the optical device coupling feature 120, one or more other features can be disposed in a wall (e.g., side wall 107, bottom wall 108) of the bottom portion 102 of the housing 101. Examples of such other features can include, but are not limited to, a light source coupling feature (for housing and/or coupling to a light source) and a power source coupling feature (for housing and/or coupling to a power source).

In cases where the bottom portion 102 has a top plate (e.g., similar to the top plate 190 of the top portion 199) or a top wall that at least substantially encloses the cavity 130, the bottom portion 102 can include one or more additional features, including but not limited to a distribution channel (e.g., similar to the distribution channel 187 of the top portion 199), and a receiving channel (e.g., similar to the receiving channel 186 of the top portion 199).

In certain example embodiments, the various coupling features (e.g., the optical device coupling feature 110, the optical device coupling feature 120, the tuning fork coupling feature 140) of the bottom portion 102 can be sized and/or arranged in a particular way, based on the characteristics of the components that couple to those coupling features, in order to achieve certain test results and/or to meet certain applicable standards. Similarly, some or all of the channels (e.g., distribution channel 187, receiving channel 186) of the top portion 199 can be sized and/or arranged in a particular way in order to achieve certain test results and/or to meet certain applicable standards.

In certain example embodiments, the bottom portion 102 of the housing 101 includes one or more of a number of coupling features 106 that allow the bottom portion 102 of the housing 101 to become coupled, directly or indirectly, to another portion (e.g., the top portion 199) of the housing 101 and/or to another component of the gas sensor module. Each coupling feature 106 can have any of a number of features and/or configurations. For example, in this case, each coupling feature 106 is an aperture that traverses the thickness of the laterally extended wall 105 of the bottom portion 102. In this case, there are two coupling features 106 that align with the coupling features 184 of the top portion 199 and are used to indirectly couple the top portion 199 and the bottom portion 102 of the housing 101 to each other using another coupling feature 193.

The coupling features 106 of the bottom portion 102 can have the same size and orientation compared to the shape and size of the coupling features 184 of the top portion 199. In this way, when the top portion 199 abuts against the bottom portion 102, the coupling features 184 and the coupling features 106 are aligned with each other so that one or more fastening devices can be disposed therein to couple the bottom portion 102 and the top portion 199 together.

In embodiments where the top portion 199 (or at least the main body 180) and the bottom portion 102 are formed from a single piece, so that the top portion 199 (or at least the main body 180) and the bottom portion 102 are permanently or fixedly coupled to each other, the coupling features 106 of the bottom portion 102 and/or the coupling features 184 of the top portion 199 can be omitted.

In certain example embodiments, a portion of the cavity of the top portion 199 of the housing 101 and/or the cavity 130 of the bottom portion 102 of the housing 101 can include one or more features that channel the flow of gas (e.g., test gas, tested gas) through that cavity or portion of the cavity. Examples of such features can include, but are not limited to, contoured inner surfaces of a wall and baffles. For example, cavity portion 159 can include baffles that channel test gas that flows from the inlet tube coupling feature 150 through the cavity portion 159 to the distribution channel 187. Such features can affect other aspects (e.g., turbulence, flow rate) of the test gas and/or tested gas.

The optical device 115 coupled to the optical device coupling feature 110 can be an assembly of one or more components (e.g., lens, light source) that uses any type of optical and/or other technology. For example, optical device 115 can be a photodiode assembly. If the optical device 115 includes a lens, the lens can be a plano-convex lens that has a focus at some point in the cavity 130. The optical device 115 can be coupled directly or indirectly to the optical device coupling feature 110. For example, the optical device 115 can include, or can be coupled to, a SubMiniature version A (SMA) connector, which in turn is coupled to the optical device coupling feature 110.

If the optical device 115 includes a light source, the light source can generate light that is directed toward the cavity 130, either directly or indirectly (e.g., through a lens) of the optical device 115. The light generated and emitted by the light source can be of any suitable wavelength, depending on one or more of a number of factors, including but not limited to the gas being tested, the temperature, and the characteristics of the lens of the optical device 115. The light source of the optical device 115 can be coupled to a power source (e.g., a driver), which can provide power and/or control signals to the light source and/or other components of the optical device 115.

The light source can include one or more of a number of components, including but not limited to a light element (e.g., a light-emitting diode, a light source, a laser diode) and a circuit board. If the optical device 115 includes a lens, the lens can be capable of receiving light (e.g., from a light source) and processing the light to create light that is transmitted to a particular location within the cavity 130. The optical device 115 can have any shape (e.g., sphere, semi-sphere, pyramid) and size that conforms to one or more contours of the optical device coupling feature 110.

The optical device 115 can be made of one or more suitable materials, including but not limited to silica and glass. In any case, the optical device 115 is resistant to corrosive materials, such as $H_2S$ gas. In order for the optical device 115 to transmit the light to a particular location within the cavity 130, a number of factors must be balanced. Such factors can include, but are not limited to, the orientation of the optical device 115, the material of the optical device 115, the position of the optical device 115 relative to the tuning fork 145 in the cavity 130, and the wavelength of the light. In certain example embodiments, a sealing member (e.g., a gasket, an o-ring, silicone) can be used to provide a barrier that prevents potentially corrosive materials in the cavity 130 from entering the optical device coupling feature 110.

The optical device 125 coupled to the optical device coupling feature 120 can be an assembly of one or more components (e.g., lens, light source) that uses any type of optical and/or other technology. The optical device 125 can be substantially the same as, or different than, the optical device 115. For example, optical device 125 can be a laser diode assembly. If the optical device 125 includes a lens, the lens can be a plano-convex lens that has a focus at some point in the cavity 130. The optical device 125 can be coupled directly or indirectly to the optical device coupling feature 120. For example, the optical device 125 can include, or can be coupled to, a SMA connector, which in turn is coupled to the optical device coupling feature 120. The optical device 125 can include one or more of a number of components, such as the components (e.g., lens, light source) described above for the optical device 115.

As discussed above, the cavity 130 of the bottom portion 102 can be formed by more than one piece. In such a case, the inner surface of the walls (e.g., side wall 107, bottom wall 108) of the pieces can be highly machined so that the junctions where the multiple pieces meet within the cavity 130 provide little to no seems that could impede the flow or the testing of the gas within the cavity 130.

In certain example embodiments, the light transmitted from an optical device (optical device 115, optical device 125), perhaps with the aid of a lens, is directed to particular point within the cavity 130. The particular point can be with respect to a portion of the tuning fork 145, described below. An example of such a particular point is approximately two-thirds up the length of a tine 147 (or between multiple tines 347) of the tuning fork 145.

The test gas that is distributed into the cavity 130 can include one or more elements (e.g., carbon, hydrogen) that can combine to form one or more compounds (e.g., methane). In some cases, the gas can also have impurities (e.g., $H_2S$) that can be detected, both in existence and in amount, using the optical gas sensor. As discussed above, the test gas can be injected into the cavity 130 through one or more channels (e.g., channel 187) disposed in the main body 180 of the top portion 199 of the housing 101, entering the cavity 130 through the second end 175 (also called a gas entry port 175) of the channel 187.

The positioning of the gas entry port 175 and/or the alignment of the channel wall 177 of the channel 187 can coincide with a reference point of or within the cavity 130. For example, in this case, the channel 187 is configured to direct the gas proximate to and along an inner surface of the inner wall 107, aligned with the optical device 115. Alternatively, the channel 187 can be configured to direct the gas at some other point or area of or within the cavity 130.

When the gas molecules interact with the light waves generated by an optical device (e.g., optical device 115, optical device 125) and directed into the cavity 130, the gas molecules become stimulated. Thus, the channel 187 is positioned and/or configured in such a way that the test gas emitted through the gas entry port 175 can more easily interact with the light waves within the cavity 130.

As discussed below, the tines 147 of the tuning fork 145, disposed in the tuning fork cavity 140, can be positioned such that the light emitted by an optical device into the cavity 130 is directed between the tines 147. The energy released by the gas molecules, stimulated by the light waves in the cavity 130, interacts with the tines 147 of the tuning fork 145. In such a case, the stimulated gas molecules change the frequency at which the tines 147 vibrate. The parameters of an optical device (or portions thereof, such as the laser) are selected so that only a particular gas can cause such interactions with the tines 147 of the tuning fork 145. In certain example embodiments, the light emitted by the optical device is directed between (in some cases, at a particular point between) the tines 147 of the tuning fork 145.

As discussed above, the tuning fork 145 (or portions thereof) can be made of quartz. The tuning fork 145, coupled to (e.g., disposed in) the tuning fork coupling feature 140 of the bottom portion 102 of the housing 101, can be any type of device that vibrates at one or more frequencies. The tuning fork 145 can have one or more components. For example, in this case, the tuning fork 145 has multiple (e.g., two) tines 147 and a base 146 from which the tines 147 extend. The tines 147 can be at least partially flexible, so that the shape of the tines 147 can change. When the shape of the tines 147 changes, the tines 147 can vibrate at a different frequency. The tuning fork 145 (including any of its components, such as the tines 147) can be made of any suitable material, including but not limited to quartz. In any case, the tuning fork 145 can be resistant to corrosive materials, such as $H_2S$ gas.

The tines 147 of the tuning fork 145 can be oriented in any of a number of suitable ways within the cavity 130. For example, the tines 147 can be substantially parallel to the inner surface of the side walls 107 that help form the cavity 130. In certain example embodiments, a sealing member (e.g., a gasket, an o-ring, silicone) (not shown) can be used to provide a barrier that prevents potentially corrosive materials in the cavity 130 from entering the tuning fork coupling feature 140. In certain example embodiments, the tines 147 of the tuning fork 145 are made of or coated with a material that is resistant to corrosive elements, such as $H_2S$.

The tines 147 of the tuning fork 145 can vibrate based on something other than the stimulated gas molecules within the cavity 130. For example, a driver (not shown) can be coupled to the tuning fork 145. In such a case, the driver can provide a vibration frequency to the tuning fork 145, causing the tines 147 to vibrate at a certain frequency. Such a frequency may be substantially similar to a frequency induced by a pure form (without any impurities) of the gas being stimulated within the cavity 130.

To measure the frequency at which the tines 147 of the tuning fork 145 are vibrating, one or more measuring devices can be used. For example, a receiver (not shown) can be coupled to the tuning fork 145. In such a case, the receiver can determine a vibration frequency to the tuning fork 145. Thus, when the vibration frequency of the tines 147 changes, the measured change can be directly correlated to an impurity in the test gas injected through the channel into the cavity 130.

The driver and/or the receiver can be coupled to the tuning fork 145 in one or more of a number of ways. For example, as shown in FIG. 1, an adapter 167 can be mechanically coupled to the base 146 of the tuning fork 145, and one or more electric conductors 166 can be coupled between the base 146 and/or the adapter 167 and the driver and/or the receiver. In certain alternative embodiments, wireless technology can be used to couple the driver and/or the receiver to the tuning fork 145.

In certain example embodiments, optical device 115 and optical device 125 each include a lens and are placed at opposite ends of the cavity 130 with the tines 147 of the tuning fork 145 in the direct linear path between the two lenses. Further, the focus of converging lenses of optical device 115 and optical device 125 lies substantially exactly in between the tines 147 of the tuning fork 145 and also at a height (e.g., two-thirds of the height of the tines 147) relative to the base 146 of the tuning fork 145. In such a case, optimal optical alignment can be achieved as all three elements (optical device 115, optical device 125, and tuning fork 145) are aligned along a central axis.

In some cases, if the two lenses of the optical devices have substantially the same focus, improved measurements of the test gas can be taken. For example, the optical alignment with a laser of one optical device (e.g., optical device 115) directed through its lens can be detected by a photo-diode of the other optical device (e.g., optical device 125) through its lens. Further, if the lenses of the optical devices are converging, maximum energy can be focused between the tines 147 of the tuning fork 145, creating a maximum interaction of a laser (light) with test gas molecules at that point, resulting in an increased sensitivity and improved measurements.

In certain example embodiments, the bottom portion 102 of the housing 101 has only a single optical device coupling feature. Alternatively, the bottom portion 102 of the housing 101 can have more than two optical device coupling features. When the bottom portion 102 of the housing 101 has two optical device coupling features, they can be aligned with each other at opposite ends of the cavity 130, as shown in FIG. 1. Alternatively, the two optical device coupling features can be disposed at any point with respect to each other in the cavity 130.

With respect to the top portion 199 of the housing 101, the inlet tube coupling feature 150 can be coupled, directly or indirectly, to an inlet tube 192. In this case, the inlet tube 192 has disposed on its distal end a threaded coupling 152 (a type of coupling feature). In such a case, the threaded coupling 152 is directly coupled to both the inlet tube coupling feature 150 and to the inlet tube 192. Similarly, the outlet tube coupling feature 155 can be coupled, directly or indirectly, to an outlet tube 191. In this case, the outlet tube 191 has disposed on its distal end a threaded coupling 157 (a type of coupling feature), which can be substantially the same as, or different than, the threaded coupling 152. In such a case, the threaded coupling 157 is directly coupled to both the outlet tube coupling feature 155 and to the outlet tube 191.

The inlet tube 192 receives test gas from some component (e.g., an inlet header) of the gas sensor or other external device, and the outlet tube 191 sends tested gas to component (e.g., an outlet header) of the gas sensor or other external device. Also, as discussed above, the top plate 190 is coupled to the main body 180 of the housing 101 using coupling features 169. In this case, the coupling features 169 are fastening devices (e.g., screws, bolts) that traverse the coupling features 198 of the top plate 190 and the coupling features 183 of the main body 180, where the coupling features 198 and the coupling features 183 are apertures.

Figure 2:
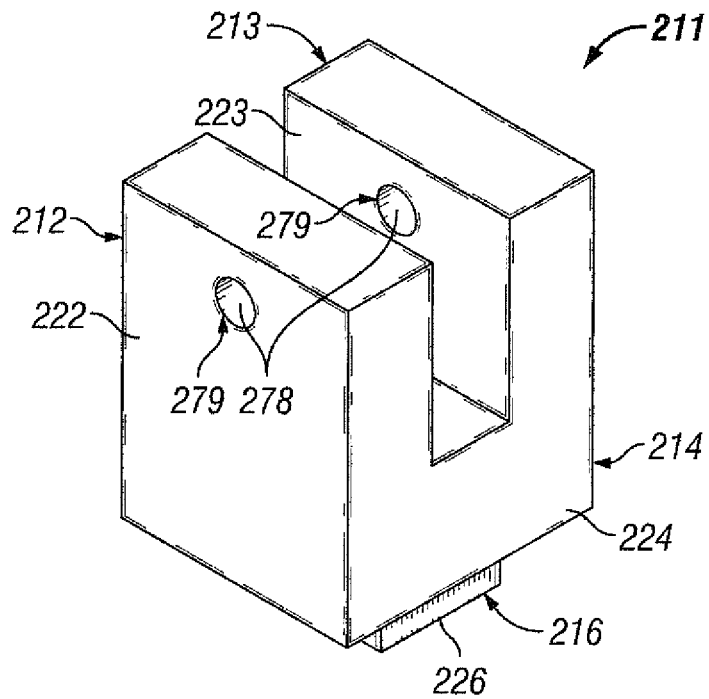
FIG. 2 shows a top-side perspective view of a module for a gas sensor in accordance with certain example embodiments.
Figure 3:
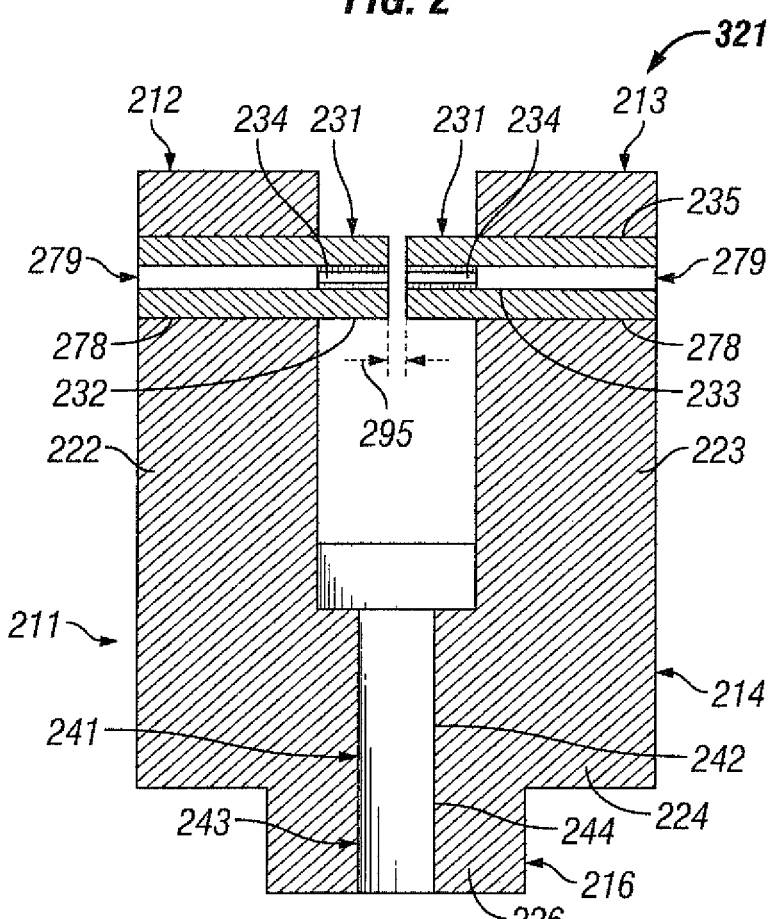
FIG. 3 shows a cross-sectional side view of a subassembly of a gas sensor that includes the module of FIG. 2 in accordance with certain example embodiments.

In some cases, enhancements to a gas sensor housing, such as the housing 101 of FIG. 1, can be made by adding one or more modules. Such modules can perform one or more of a number of functions. Examples of such functions can include, but are not limited to, better alignment of the tuning fork 145, more precise intersection of light emitted by an optical device (e.g., optical device 115, optical device 125) and the tines 147 of the tuning fork 145, and improved amplification of the signal detected by the sensor module. FIGS. 2 and 3 show an example embodiment of such a module. FIG. 2 shows a top-side perspective view of a module 211 for a gas sensor in accordance with certain example embodiments. FIG. 3 shows a cross-sectional side view of a subassembly 321 of a gas sensor that includes the module 211 of FIG. 2 in accordance with certain example embodiments.

Referring to FIGS. 1-3, a module can have one or more portions and/or can be in one or more pieces. For example, in this case, the module 211 is a single piece that has four portions (portion 212, portion 213, portion 214, and portion 216). Each portion of a module can have one or more of a number of features, including coupling features. For example, as shown in FIGS. 2 and 3, portion 212 can include at least one micro-resonator coupling feature 279. The micro-resonator coupling feature 279 can take any of a number of shapes and/or forms. For example in this case, the micro-resonator coupling feature 279 is an aperture formed by a wall 278 that traverses the thickness of the body 222 of portion 212.

The micro-resonator coupling feature 279 can couple to (e.g., receive) a micro-resonator 231. The micro-resonator coupling feature 279 can include any of a number of features (e.g., a collar, a notch, a protrusion, a recess) to help in coupling a micro-resonator 231 with the micro-resonator coupling feature 279. In certain example embodiments, a micro-resonator 231 (also called a microresonator 231) is one or more devices that each form an elongated tube having an inner surface 233 and an outer surface 235. The micro-resonator 231 can have a length that is at least as great as the thickness of the body 222 of portion 212.

A micro-resonator 231 can also include one or more resonating elements 234. In this case, a resonating element 234 is disposed at a distal end of the micro-resonator 212, within the cavity formed by the inner surface 233. In such a case, the resonating element 231 is disposed adjacent to the tines of a tuning fork. The micro-resonator 231 can be disposed in the micro-resonator coupling feature 279 of portion 212 of the module 211 so that the light emitted by an optical device (e.g., optical device 125) can travel therethrough before reaching the tines of a tuning fork.

Specifically, the micro-resonator 231 can be a small-scale structure or group of structures that are designed to confine and/or otherwise manipulate light. The light is reflected internally along the inner surface 233 of the micro-resonator 231. This creates a series of standing-wave optical modes, or resonances, similar to those that can exist on a vibrating guitar string. The micro-resonators 231 can thus also be used in this case to align the tuning fork and allow for more precise measurements. The micro-resonator 231 (or portions thereof) can be part of, or separate from, an optical device (e.g., optical device 115, optical device 125). Thus, the micro-resonator coupling feature 279 of portion 212 is configured to allow the micro-resonator 279, when coupled to the micro-resonator coupling feature 279, to be properly aligned with an optical device.

When the micro-resonators 231 are coupled to the micro-resonator coupling features 279 of portion 212 and portion 213, there is a gap 295 between the distal ends of the micro-resonators 231. The gap 295 is configurable to be wide enough to allow one or more tines of a tuning fork be disposed therebetween when the tuning fork is coupled to the module 211.

Portion 212 and portion 213 of the module 211 of FIG. 2 are substantially identical to each other. Specifically, the body 223 of portion 213 has substantially the same characteristics (e.g., length, thickness, height) as the body 222 of portion 212. Further, portion 213 can have a micro-resonator coupling feature 279 that traverses the thickness of the body 223. The micro-resonator 231 (the same micro-resonator or a separate micro-resonator relative to the micro-resonator 231 coupled to the micro-resonator coupling feature 279 of portion 212) can be coupled to the micro-resonator coupling feature 279 of portion 213 and positioned between the tuning fork and another optical device (e.g., optical device 115). While the micro-resonator coupling feature 279 of portion 213 is substantially the same as the micro-resonator coupling feature 279 of portion 212, they can also be different from each other.

In such a case, the light that passes through the tines of the tuning fork can continue to pass through the micro-resonator 231 to the other optical device, where the light is measured. In certain example embodiments, the micro-resonator coupling feature 279 of portion 213 can be oriented in such a way that the micro-resonator 231 coupled to the micro-resonator coupling feature 279 of portion 213 is substantially aligned with the micro-resonator 231 coupled to the micro-resonator coupling feature 279 of portion 212.

Portion 214 of the module 211 of FIGS. 2 and 3 can act as a base from which portion 212 and portion 213 extend. The body 224 of portion 214 can have any suitable characteristics (e.g., length, thickness, height) based on the corresponding characteristics of portion 212 and/or portion 213. As discussed above, portion 212, portion 213, and portion 214 can be separate pieces or part of a single piece. Portion 214 can include one or more of a number of coupling features. For example, in this case, portion 214 includes a tuning fork coupling feature 241.

The tuning fork coupling feature 241 can take any of a number of shapes and/or forms. For example in this case, the tuning fork coupling feature 241 is an aperture formed by a wall 242 that traverses the thickness of the body 224 of portion 214. The tuning fork coupling feature 241 can couple to (e.g., receive) at least a portion of a tuning fork (e.g., tuning fork 145). The tuning fork coupling feature 241 can include any of a number of features (e.g., a collar, a notch, a protrusion, a recess) to help in coupling a tuning fork with the tuning fork coupling feature 241. For example, the tuning fork coupling feature 241 can couple to a base (e.g., base 146) of a tuning fork. In certain example embodiments, the tuning fork coupling feature 241 is substantially perpendicular to the micro-resonator coupling features 279.

Portion 216 of the module 211 of FIGS. 2 and 3 can extend from the bottom of the body 224 of portion 214. Portion 216 can couple to (e.g., be disposed within) a tuning fork coupling feature (e.g., tuning fork coupling feature 140) of a gas sensor housing (e.g., gas sensor housing 101) of a gas sensor. As such, the body 226 of portion 216 can have one or more coupling features (e.g., mating threads, protrusions, recesses, slots) that allow portion 216 to couple to the tuning fork coupling feature of a gas sensor housing.

Further, the body 226 of portion 216 can have any suitable characteristics (e.g., length, thickness, height) based on the corresponding characteristics of portion 214 of the module 211 and/or the corresponding characteristics of a tuning fork coupling feature of a housing of the gas sensor. As discussed above, portion 212, portion 213, portion 214, and/or portion 216 can be separate pieces or part of a single piece. Portion 216 can include one or more of a number of coupling features. For example, in this case, portion 216 includes a tuning fork coupling feature 243.

The tuning fork coupling feature 243 can take any of a number of shapes and/or forms. For example in this case, the tuning fork coupling feature 243 is an aperture formed by a wall 244 that traverses the thickness of the body 226 of portion 216. The tuning fork coupling feature 243 can couple to (e.g., receive) at least a portion of a tuning fork (e.g., tuning fork 145). The tuning fork coupling feature 243 can include any of a number of features (e.g., a collar, a notch, a protrusion, a recess) to help in coupling a tuning fork with the tuning fork coupling feature 243. In certain example embodiments, the tuning fork coupling feature 243 of portion 216 can be aligned with and have substantially the same characteristics as the tuning fork coupling feature 241 of portion 214.

Figure 4A:
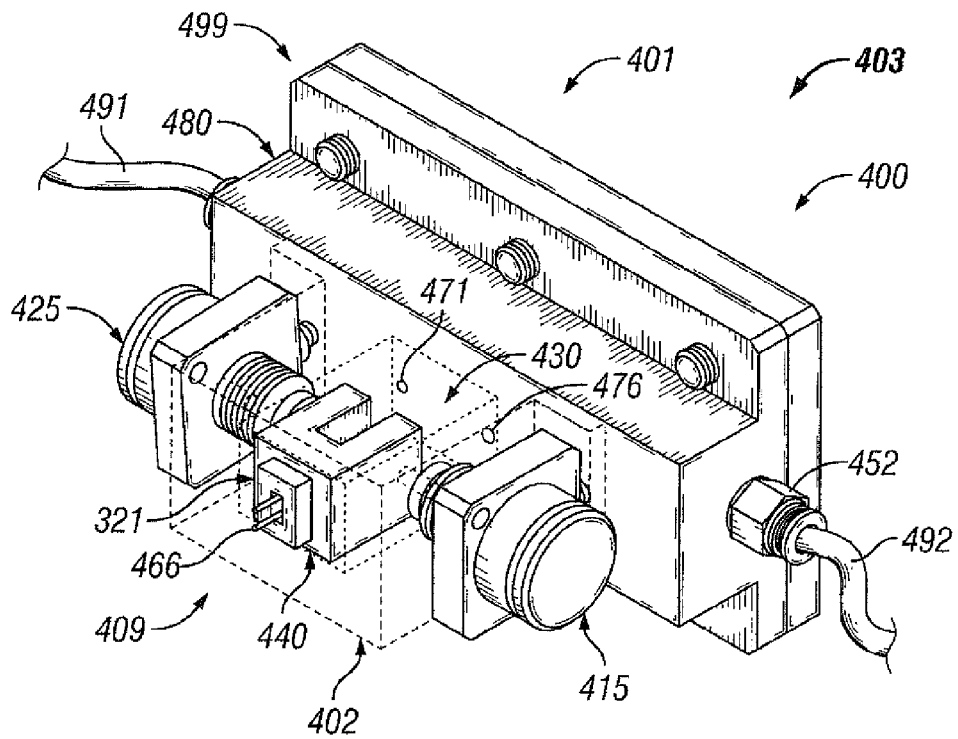
FIGS. 4A and 4B show another subassembly of a gas sensor that includes the subassembly of FIG. 3 in accordance with certain example embodiments.
Figure 4B:
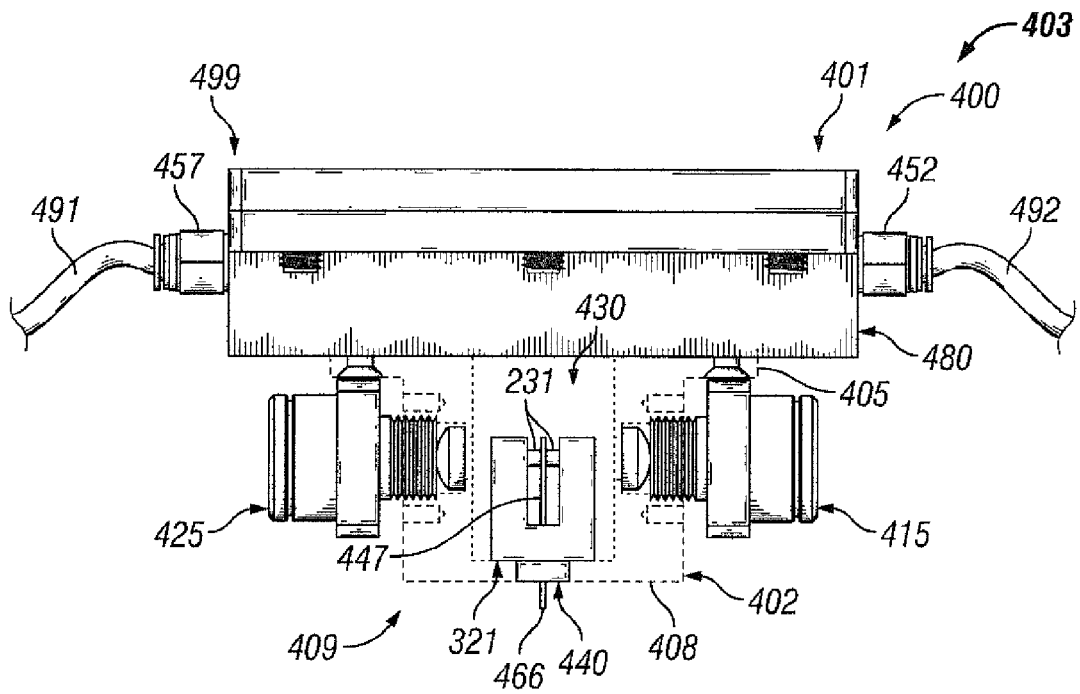
Figure 5A:
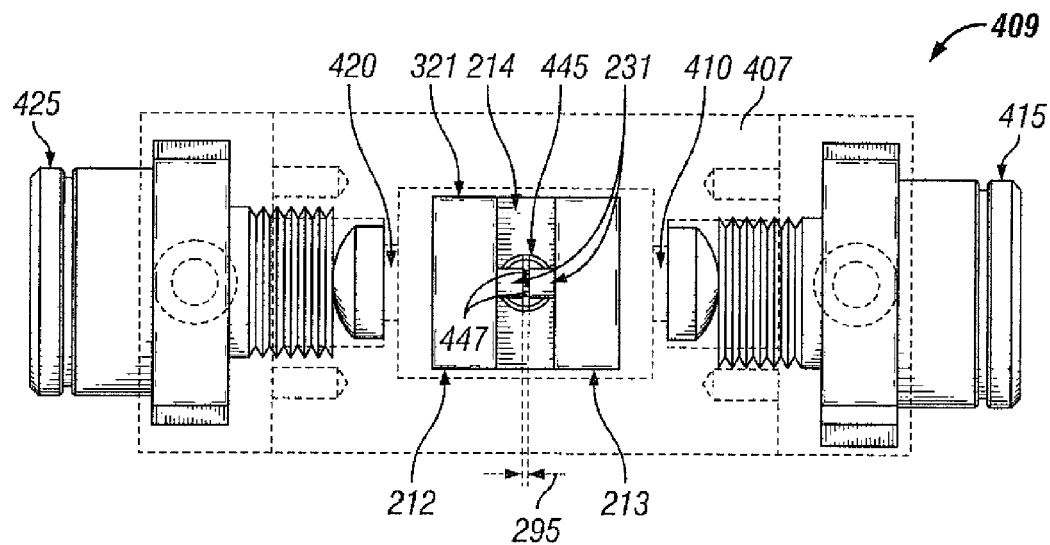
FIGS. 5A and 5B show detailed views of the subassembly of FIGS. 4A and 4B in accordance with certain example embodiments.
Figure 5B:
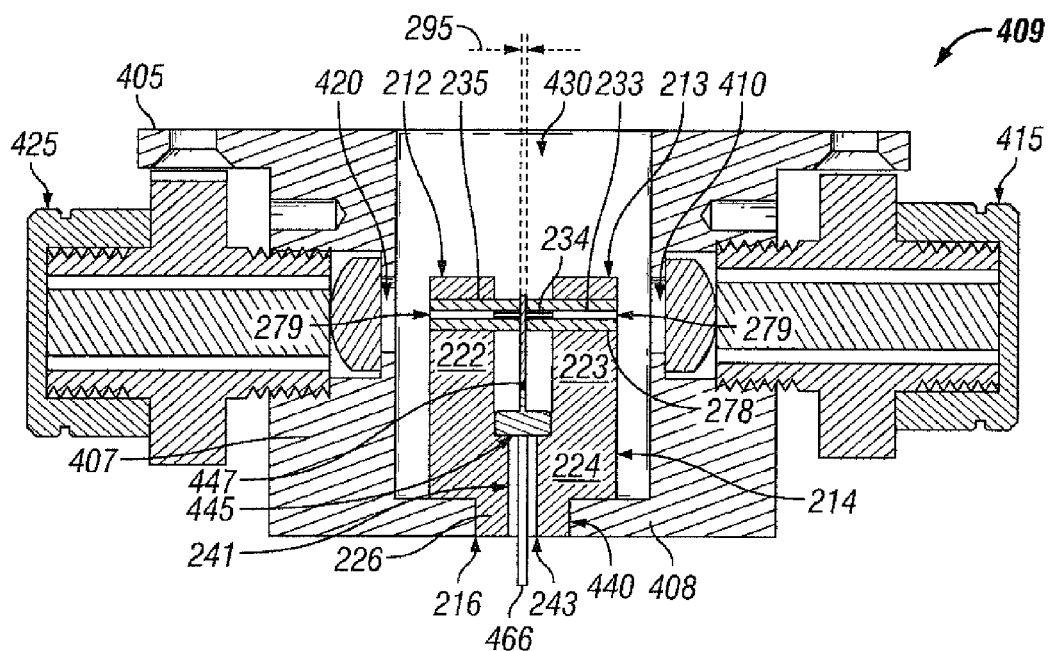

FIGS. 4A and 4B show a subassembly 403 of a gas sensor that includes the subassembly 321 of FIG. 3 and a subassembly 400, which is substantially similar to the subassembly 100 of FIG. 1, in accordance with certain example embodiments. FIGS. 5A and 5B show detailed views of a portion 409 of the subassembly 403 of FIGS. 4A and 4B in accordance with certain example embodiments. Referring to FIGS. 1-5B, the subassembly 321 of FIG. 3 is disposed, at least in part, within the cavity 430 of the bottom portion 402 of the housing 401. Portion 216 is coupled to the tuning fork coupling feature 440 of the bottom portion 402 of the housing 401.

When the subassembly 321 (and, more specifically, the module 211) is disposed within the cavity 430 of the bottom portion 402 of the housing 401, the tuning fork coupling feature 440 of the housing 401 can be referred to as a module coupling feature 440 for directly coupling to the module 211, which is directly coupled to the tuning fork 445. Specifically, in this case, the tuning fork 445 is coupled to the tuning fork coupling feature 241 of portion 214 and the tuning fork coupling feature 243 of portion 216 of the module 211.

Further, the micro-resonator coupling feature 279 of portion 212 is configured in such a way that the micro-resonator 231 coupled to the micro-resonator coupling feature 279 of portion 212 directs light emitted by the optical device 425 toward the tines 447 of the tuning fork 445. Also, the micro-resonator coupling feature 279 of portion 213 is configured in such a way that the micro-resonator 231 coupled to the micro-resonator coupling feature 279 of portion 213 directs light emitted through the tines 447 of the tuning fork 445 toward the optical device 415. The tines 447 of the tuning fork 445 are disposed within the gap 295 between the distal ends of the micro-resonators 231.

As discussed above, example modules described herein can have a number of shapes, sizes, pieces, and other characteristics. An example of another module 911 is shown in FIGS. 6A-9. FIGS. 6A and 6B show a back-side perspective view and a side view, respectively, of a portion 612 of the 911 module for a gas sensor in accordance with certain example embodiments. FIGS. 7A and 7B show a back-side perspective view and a side view, respectively, of another portion 713 of the 911 module in accordance with certain example embodiments. FIGS. 8A-8C show a top-side perspective view, a side view, and a cross-sectional side view, respectively, of a yet another portion 814 of the module 911 in accordance with certain example embodiments. FIG. 9 shows a side view of the module 911 in accordance with certain example embodiments.

In this example embodiment, the module 911 includes three pieces, where each piece has at least one portion. Each piece of the module 911 can have one or more of a number of features, including coupling features. For example, as shown in FIGS. 6A and 6B, portion 612 can include at least one micro-resonator coupling feature 679. The micro-resonator coupling feature 679 can take any of a number of shapes and/or forms. For example in this case, the micro-resonator coupling feature 679 is an aperture formed by a wall 678 that traverses the thickness of the upper portion of the body 622 of portion 612.

The micro-resonator coupling feature 679 can couple to (e.g., receive) some or all of a micro-resonator (not shown, but substantially similar to the micro-resonator 231 described above). The micro-resonator coupling feature 679 can include any of a number of features (e.g., a collar, a notch, a protrusion, a recess) to help in coupling a micro-resonator with the micro-resonator coupling feature 679. The micro-resonator can have a length that is at least as great as the thickness of the body 622 of portion 612. In addition, portion 612 can have one or more other features. For example, as shown in FIGS. 6A and 6B, the body 622 of portion 612 can have a stepped arrangement so that portion 612 can couple to (e.g., abut against) portion 814.

Portion 713 can also include at least one micro-resonator coupling feature 779. The micro-resonator coupling feature 779 can take any of a number of shapes and/or forms. For example in this case, the micro-resonator coupling feature 779 is an aperture formed by a wall 778 that traverses the thickness of the upper portion of the body 722 of portion 712. In other words, the micro-resonator coupling feature 779 of portion 713 can be substantially the same as the micro-resonator coupling feature 679 of portion 612.

The micro-resonator coupling feature 779 can couple to (e.g., receive) some or all of a micro-resonator (not shown, but substantially similar to the micro-resonator 231 described above). The micro-resonator coupling feature 779 can include any of a number of features (e.g., a collar, a notch, a protrusion, a recess) to help in coupling a micro-resonator with the micro-resonator coupling feature 779. The micro-resonator can have a length that is at least as great as the thickness of the body 722 of portion 713. In addition, portion 713 can have one or more other features. For example, as shown in FIGS. 7A and 7B, the body 722 of portion 713 can have a stepped arrangement so that portion 713 can couple to (e.g., abut against) portion 814.

While portion 612 and portion 713 can have different features and/or characteristics with respect to each other, portion 612 and portion 713 of the module 911 shown in FIGS. 6A-9 are substantially identical to each other and oriented as mirror images with respect to each other. Specifically, the body 723 of portion 713 has substantially the same characteristics (e.g., length, thickness, height) as the body 622 of portion 612. A micro-resonator can be coupled to the micro-resonator coupling feature 679 of portion 612 and positioned between the tuning fork and an optical device (e.g., optical device 1025 of FIGS. 10A-11B below).. Similarly, another micro-resonator (or the same micro-resonator) can be coupled to the micro-resonator coupling feature 779 of portion 713 and positioned between the tuning fork and another optical device (e.g., optical device 1015 of FIGS. 10A-11B below).

In such a case, the light emitted by an optical device (e.g., optical device 1025) passes through one micro-resonator, through the tines (e.g., tines 1047 below) of a tuning fork (e.g., tuning fork 1045 below) disposed between portion 612 and portion 713, and continues through another micro-resonator to another optical device (e.g., optical device 1015), where the light is measured. In certain example embodiments, the micro-resonator coupling feature 779 of portion 713 can be oriented in such a way that the micro-resonator coupled to the micro-resonator coupling feature 779 of portion 713 is substantially aligned with the micro-resonator coupled to the micro-resonator coupling feature 679 of portion 612.

Portion 814 of the module 911 of FIGS. 8A-9 can act as a base from which portion 612 and portion 713 couple to (e.g., abut against). The body 824 of portion 814 can have any suitable characteristics (e.g., length, thickness, height) based on the corresponding characteristics of portion 612 and/or portion 713. As discussed above, portion 612, portion 713, and portion 814 can be separate pieces (as in this example) or part of a single piece. Portion 814 can include one or more of a number of coupling features. For example, in this case, portion 814 includes a tuning fork coupling feature 841.

The tuning fork coupling feature 841 of portion 814 can take any of a number of shapes and/or forms. For example in this case, the tuning fork coupling feature 841 is an aperture formed by a wall 842 that traverses the thickness of the body 824 of portion 814. The tuning fork coupling feature 841 can couple to (e.g., receive) at least a portion of a tuning fork (e.g., tuning fork 1045 below). The tuning fork coupling feature 841 can include any of a number of features (e.g., a collar, a notch, a protrusion, a recess) to help in coupling a tuning fork with the tuning fork coupling feature 841. For example, the tuning fork coupling feature 841 can couple to a base of a tuning fork. In certain example embodiments, the tuning fork coupling feature 641 is substantially perpendicular to the micro-resonator coupling feature 679 and the micro-resonator coupling feature 779 when the various portions of the module 911 are coupled to each other.

Portion 816 of the module 911 of FIGS. 8A-9 can extend from the bottom of the body 824 of portion 814. Portion 816 can couple to (e.g., be disposed within) a tuning fork coupling feature (e.g., tuning fork coupling feature 1040, also called a module coupling feature 1040 below) of a gas sensor housing (e.g., gas sensor housing 1001 below) of a gas sensor. As such, the body 826 of portion 816 can have one or more coupling features (e.g., mating threads, protrusions, recesses, slots) that allow portion 816 to couple to the tuning fork coupling feature of a gas sensor housing.

Further, the body 826 of portion 816 can have any suitable characteristics (e.g., length, thickness, height) based on the corresponding characteristics of portion 814 of the module 911 and/or the corresponding characteristics of a tuning fork coupling feature of a housing of the gas sensor. As discussed above, portion 612, portion 713, portion 814, and/or portion 816 can be separate pieces or part of a single piece. Portion 816 can include one or more of a number of coupling features. For example, in this case, portion 816 includes a tuning fork coupling feature 843.

The tuning fork coupling feature 843 can take any of a number of shapes and/or forms. For example in this case, the tuning fork coupling feature 843 is an aperture formed by a wall 844 that traverses the thickness of the body 826 of portion 816. The tuning fork coupling feature 843 can couple to (e.g., receive) at least a portion of a tuning fork (e.g., tuning fork 1045). The tuning fork coupling feature 843 can include any of a number of features (e.g., a collar, a notch, a protrusion, a recess) to help in coupling a tuning fork with the tuning fork coupling feature 843. In certain example embodiments, the tuning fork coupling feature 843 of portion 816 can be aligned with and have substantially the same characteristics as the tuning fork coupling feature 841 of portion 814.

In this example, the micro-resonators are disposed completely within the micro-resonator coupling features 679 of portion 612 and the micro-resonator coupling features 779 of portion 713. As shown in FIG. 9, when portion 612 and portion 713 are coupled to (e.g., abut against) portion 814, there is a gap 995 between the distal ends of the micro-resonators, which can also correspond to the distal end of the micro-resonator coupling features 679 and the micro-resonator coupling features 779. The gap 995 is configurable to be wide enough to allow one or more tines of a tuning fork be disposed therebetween when the tuning fork is coupled to the module 911. Portion 612, portion 713, and/or portion 814 of the module 911 can include one or more coupling features that allow one portion to couple to one or more other portions of the module 911. For example, in this case, the coupling features of the portions are merely the outer surfaces of the bodies of those portions as they couple to (abut against) the outer surface of a body of an adjacent portion of the module 911.

Figure 10A:
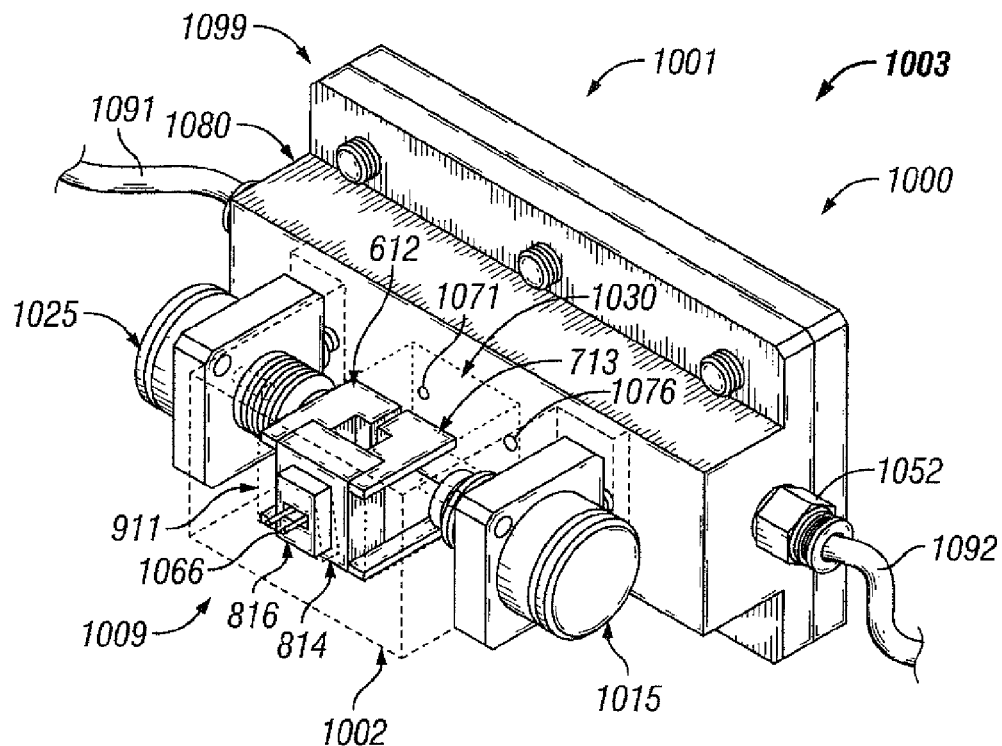
FIGS. 10A and 10B show another subassembly of a gas sensor that includes the module of FIGS. 6A-9 in accordance with certain example embodiments.
Figure 10B:
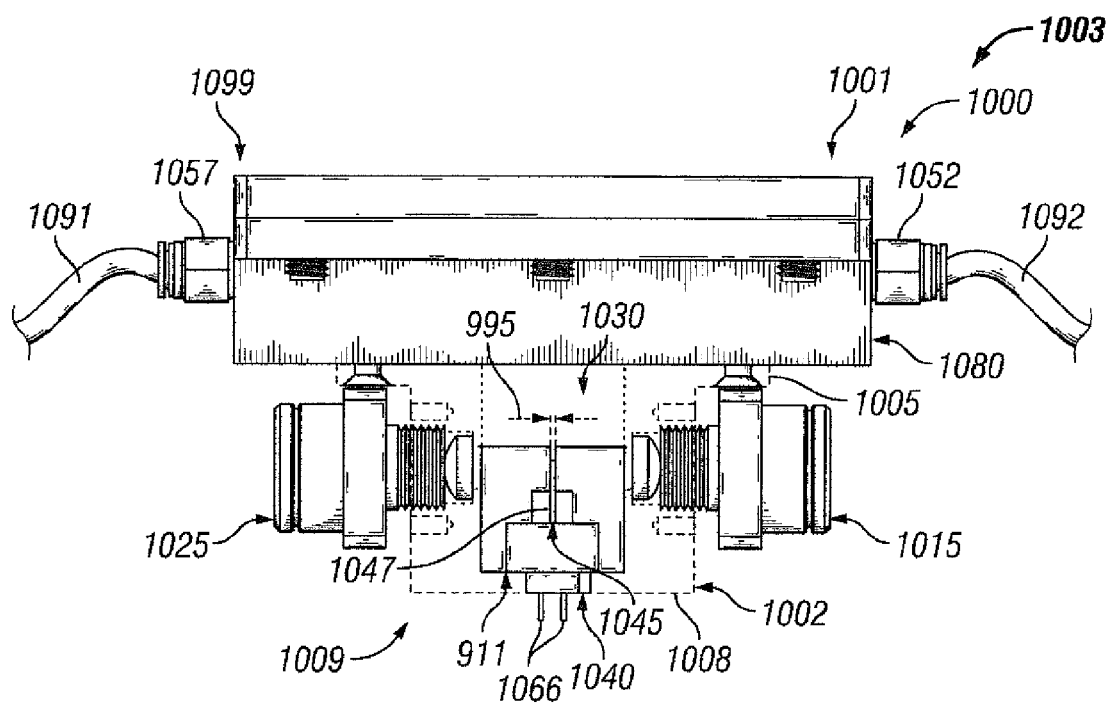
Figure 11A:
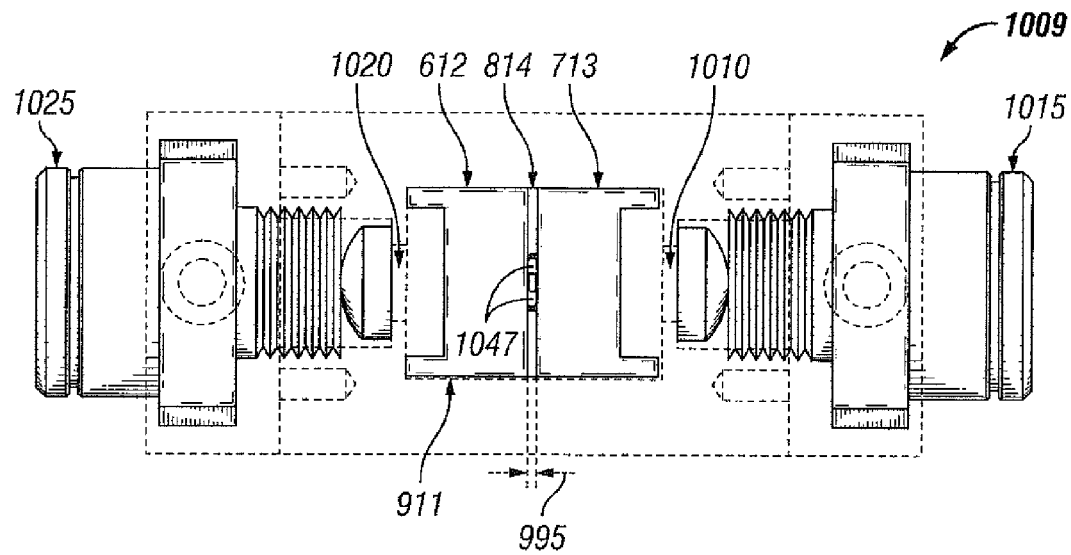
FIGS. 11A and 11B show detailed views of the subassembly of FIGS. 10A and 10B in accordance with certain example embodiments.
Figure 11B:
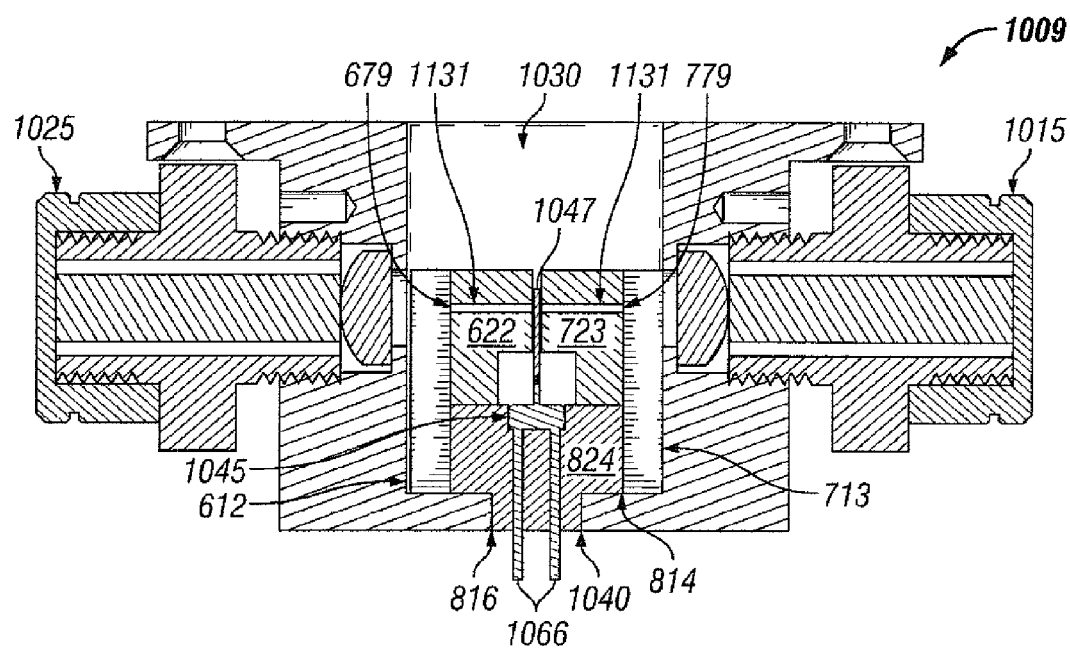

FIGS. 10A and 10B show a subassembly 1003 of a gas sensor that includes the module 911 of FIGS. 6A-9 and a subassembly 1000, which is substantially similar to the subassembly 100 of FIG. 1, in accordance with certain example embodiments. FIGS. 11A and 11B show detailed views of a portion 1009 of the subassembly 1003 of FIGS. 10A and 10B in accordance with certain example embodiments. Referring to FIGS. 1-11B, the module 911 of FIG. 9 is disposed, at least in part, within the cavity 1030 of the bottom portion 1002 of the housing 1001. Portion 816 is coupled to the tuning fork coupling feature 1040 (also called the module coupling feature 1040) of the bottom portion 1002 of the housing 1001. In addition, the tuning fork 1045 is coupled to the tuning fork coupling feature 841 of portion 814 and the tuning fork coupling feature 843 of portion 816 of the module 911.

Further, the micro-resonator coupling feature 679 of portion 612 is configured in such a way that a micro-resonator (hidden from view) coupled to the micro-resonator coupling feature 679 of portion 612 directs light emitted by the optical device 1025 toward the tines 1047 of the tuning fork 1045. Also, the micro-resonator coupling feature 779 of portion 713 is configured in such a way that another micro-resonator (also hidden from view) coupled to the micro-resonator coupling feature 779 of portion 713 directs light emitted through the tines 1047 of the tuning fork 1045 toward the optical device 1015. The tines 1047 of the tuning fork 1045 are disposed within the gap 995 between the distal ends of the micro-resonators (which, in this case, coincides with the distal ends of the micro-resonator coupling feature 679 of portion 612 and the micro-resonator coupling feature 779 of portion 713.

Figure 12A:
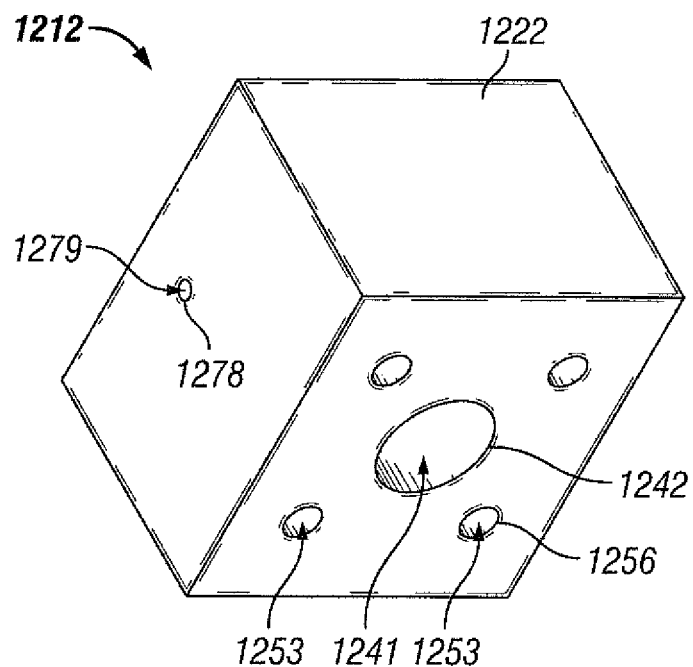
FIGS. 12A and 12B show a portion of a module for a gas sensor in accordance with certain example embodiments.
Figure 12B:
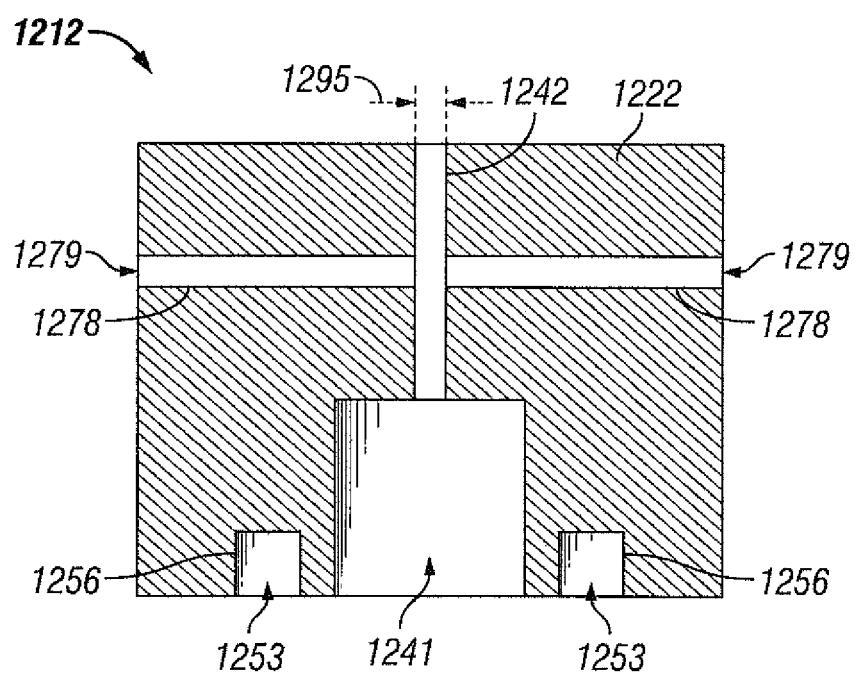
Figure 13A:
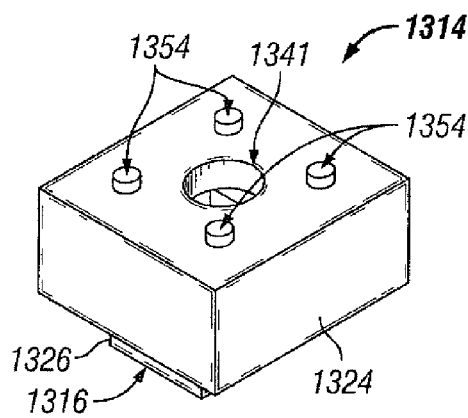
FIGS. 13A-13C show another portion of a module for a gas sensor in accordance with certain example embodiments.
Figure 13B:
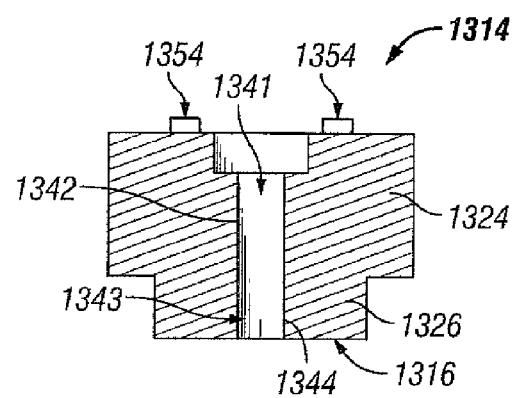
Figure 13C:
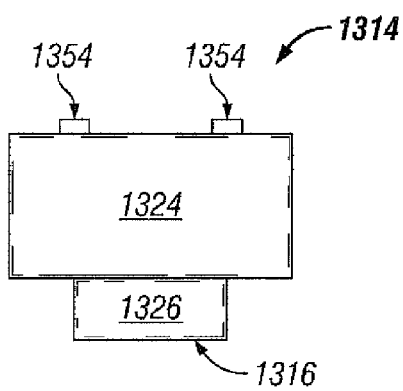
Figure 14:
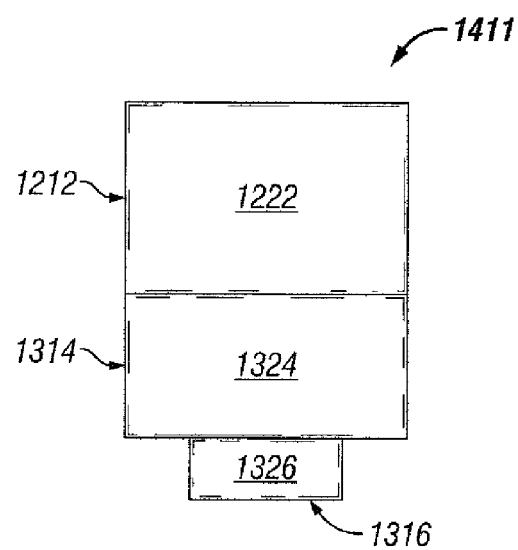
FIG. 14 shows a side view of a module for a gas sensor that includes the portions of FIGS. 12A-13C in accordance with certain example embodiments.

An example of yet another module 1411 is shown in FIGS. 12A-14. FIGS. 12A and 12B show a bottom-side perspective view and a cross-sectional side view, respectively, of a portion 1212 of the 1411 module for a gas sensor in accordance with certain example embodiments. FIGS. 13A-13C show a top-side perspective view, a cross-sectional side view, and a side view, respectively, of another portion 1314 of the 1411 module in accordance with certain example embodiments. FIG. 14 shows a side view of the module 1411 in accordance with certain example embodiments.

In this example embodiment, the module 1411 includes two pieces, where each piece has at least one portion. Each piece of the module 1411 can have one or more of a number of features, including coupling features. For example, as shown in FIGS. 12A and 12B, portion 1212 can include at least one micro-resonator coupling feature 1279. A micro-resonator coupling feature 1279 can take any of a number of shapes and/or forms. For example in this case, each micro-resonator coupling feature 1279 is an aperture formed by a wall 1278 that traverses a portion of the thickness of the body 1222 of portion 1212.

The micro-resonator coupling feature 1279 can couple to (e.g., receive) some or all of a micro-resonator (not shown, but substantially similar to the micro-resonator 231 described above). The micro-resonator coupling feature 1279 can include any of a number of features (e.g., a collar, a notch, a protrusion, a recess) to help in coupling a micro-resonator with the micro-resonator coupling feature 1279. In this case, the micro-resonator can have a length that is substantially the same as the length of the micro-resonator coupling feature 1279.

In certain example embodiments, the micro-resonator coupling features 1279 of portion 1212 of FIGS. 12A and 12B are positioned adjacent to a tuning fork coupling feature 1241 of portion 1212. The tuning fork coupling feature 1241 of portion 1212 can take any of a number of shapes and/or forms. For example in this case, the tuning fork coupling feature 1241 is an aperture formed by a wall 1242 that traverses the thickness of the body 1222 of portion 1212. The tuning fork coupling feature 1241 can couple to (e.g., receive) at least a portion of a tuning fork (e.g., tuning fork 1545 below). The tuning fork coupling feature 1241 can include any of a number of features (e.g., a collar, a notch, a protrusion, a recess) to help in coupling a tuning fork with the tuning fork coupling feature 1241. For example, the tuning fork coupling feature 1241 can couple to a base of a tuning fork. In certain example embodiments, the tuning fork coupling feature 141 is substantially perpendicular to the micro-resonator coupling features 1279.

In certain example embodiments, the wall of a tuning fork coupling feature described herein does not directly contact any portion of the tuning fork. For example, the wall 1242 may not directly contact any portion of the tuning fork disposed in the tuning fork coupling feature 1241. In such a case, the tuning fork coupling feature 1241 can simply be referred to as an aperture 1241. In any case, the width of the tuning fork coupling feature 1241 (or the aperture 1241) at the point where micro-resonator coupling features 1279 intersect the tuning fork coupling feature 1241 defines the gap 1295 between the micro-resonator coupling features 1279. If the micro-resonators coupled to (disposed within) the micro-resonator coupling features 1279 are even with the distal ends of the micro-resonator coupling features 1279, then the gap 1295 also defines the distance between the micro-resonators.

Portion 1212 can have one or more other coupling features. For example, as shown in FIGS. 12A and 12B, the body 1222 of portion 1212 can include one or more module coupling features 1253 that are used to couple portion 1212 to one or more module coupling features 1354 of portion 1314. In this case, the module coupling features 1253 of portion 1212 are cylindrical recesses in the bottom surface of the body 1222, and module coupling features 1354 of portion 1314 are cylindrical protrusions that extend from the top surface of the body 1324 of portion 1314.

In addition, portion 1314 can include a tuning fork coupling feature 1341. The tuning fork coupling feature 1341 of portion 1314 can take any of a number of shapes and/or forms. For example in this case, the tuning fork coupling feature 1341 is an aperture formed by a wall 1243 that traverses the thickness of the body 1324 of portion 1314. The tuning fork coupling feature 1341 can couple to (e.g., receive) at least a portion of a tuning fork. The tuning fork coupling feature 1341 can include any of a number of features (e.g., a collar, a notch, a protrusion, a recess) to help in coupling a tuning fork with the tuning fork coupling feature 1341. For example, the tuning fork coupling feature 1341 can couple to a base of a tuning fork. In certain example embodiments, the tuning fork coupling feature 1341 of portion 1314 can be aligned with and have substantially the same characteristics as the tuning fork coupling feature 1241 of portion 1212.

Portion 1316 of the module 1411 of FIGS. 13A-14 can extend from the bottom of the body 1324 of portion 1314. Portion 1316 can couple to (e.g., be disposed within) a tuning fork coupling feature (e.g., tuning fork coupling feature 1540, also called a module coupling feature 1540, below) of a gas sensor housing (e.g., gas sensor housing 1501 below) of a gas sensor. As such, the body 1326 of portion 1316 can have one or more coupling features (e.g., mating threads, protrusions, recesses, slots) that allow portion 1316 to couple to the tuning fork coupling feature of a gas sensor housing.

Further, the body 1326 of portion 1316 can have any suitable characteristics (e.g., length, thickness, height) based on the corresponding characteristics of portion 1314 of the module 1411 and/or the corresponding characteristics of a tuning fork coupling feature of a housing of the gas sensor. As discussed above, portion 1212, portion 1314, and/or portion 1316 can be separate pieces or part of a single piece. Portion 1316 can include one or more of a number of coupling features. For example, in this case, portion 1316 includes a tuning fork coupling feature 1343.

The tuning fork coupling feature 1343 can take any of a number of shapes and/or forms. For example in this case, the tuning fork coupling feature 1343 is an aperture formed by a wall 1344 that traverses the thickness of the body 1326 of portion 1316. The tuning fork coupling feature 1343 can couple to (e.g., receive) at least a portion of a tuning fork (e g, tuning fork 1545). The tuning fork coupling feature 1343 can include any of a number of features (e.g., a collar, a notch, a protrusion, a recess) to help in coupling a tuning fork with the tuning fork coupling feature 1343. In certain example embodiments, the tuning fork coupling feature 1343 of portion 1316 can be aligned with and have substantially the same characteristics as the tuning fork coupling feature 1341 of portion 1314.

Figure 15A:
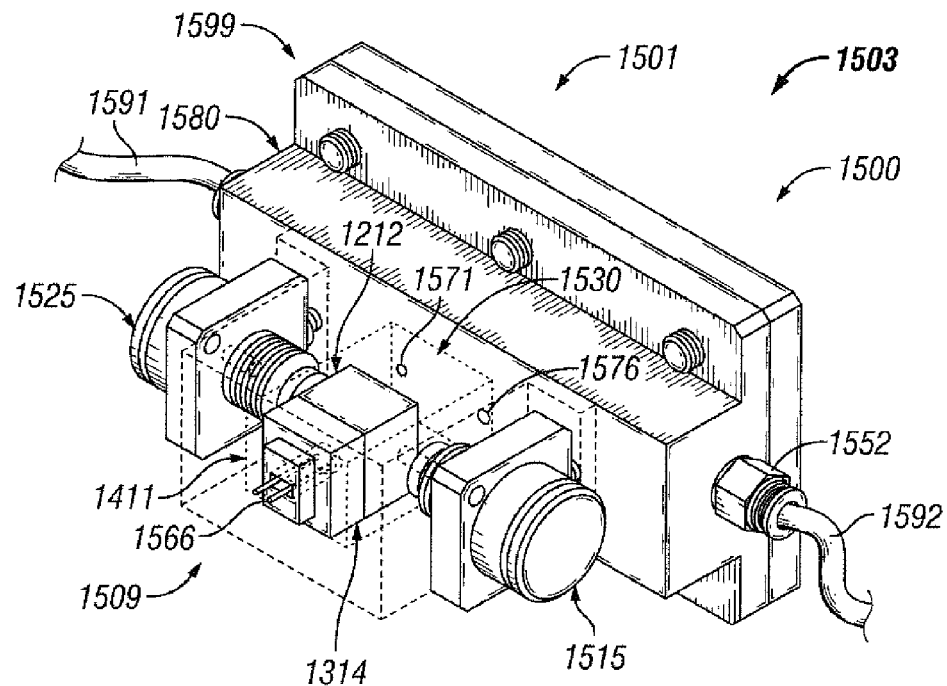
FIGS. 15A and 15B show another subassembly of a gas sensor that includes the module of FIGS. 12A-14 in accordance with certain example embodiments.
Figure 15B:
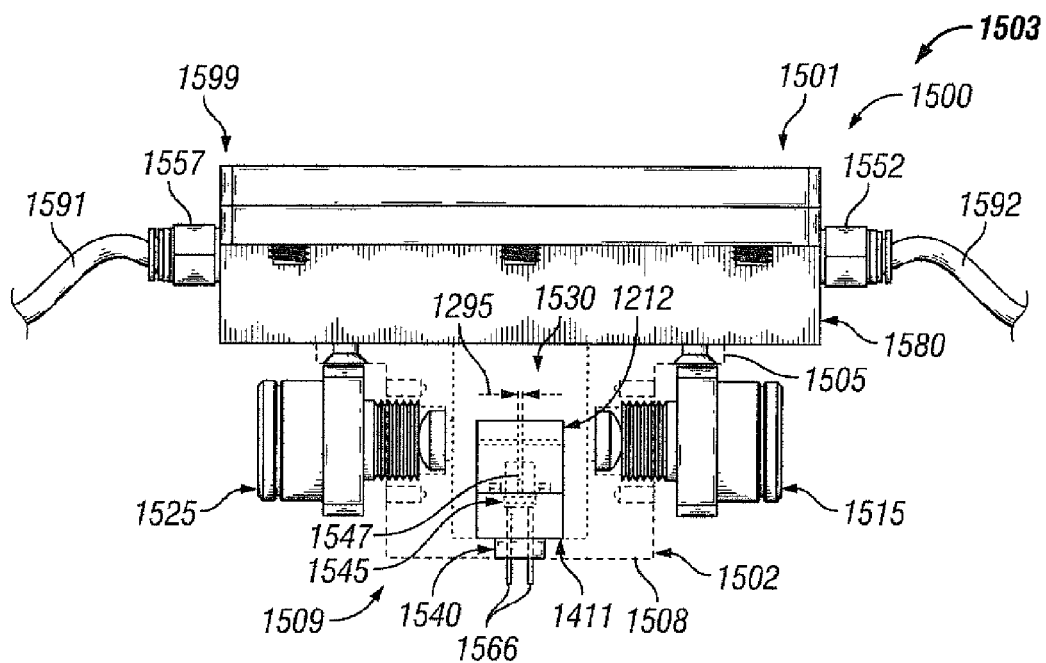
Figure 16A:
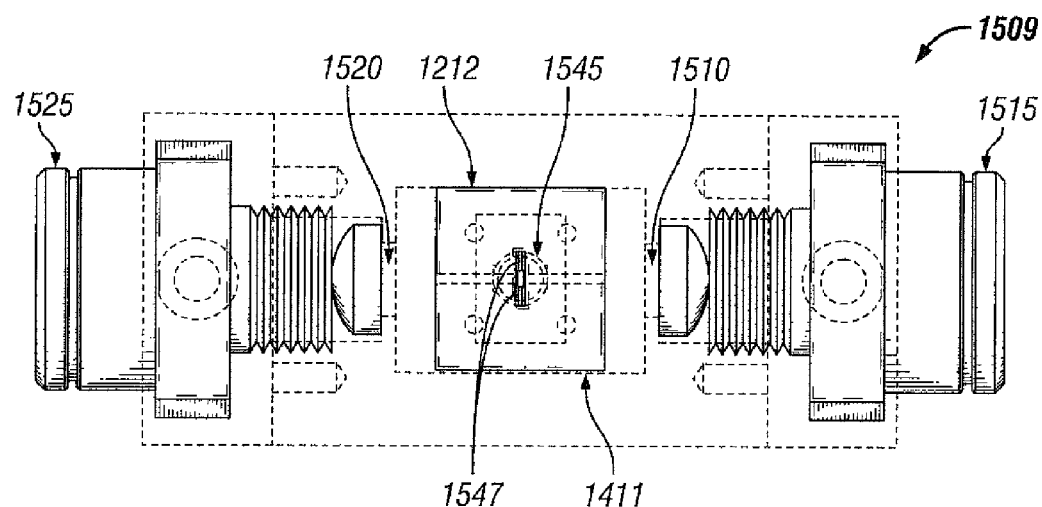
FIGS. 16A and 16B show detailed views of the subassembly of FIGS. 15A and 15B in accordance with certain example embodiments.
Figure 16B:
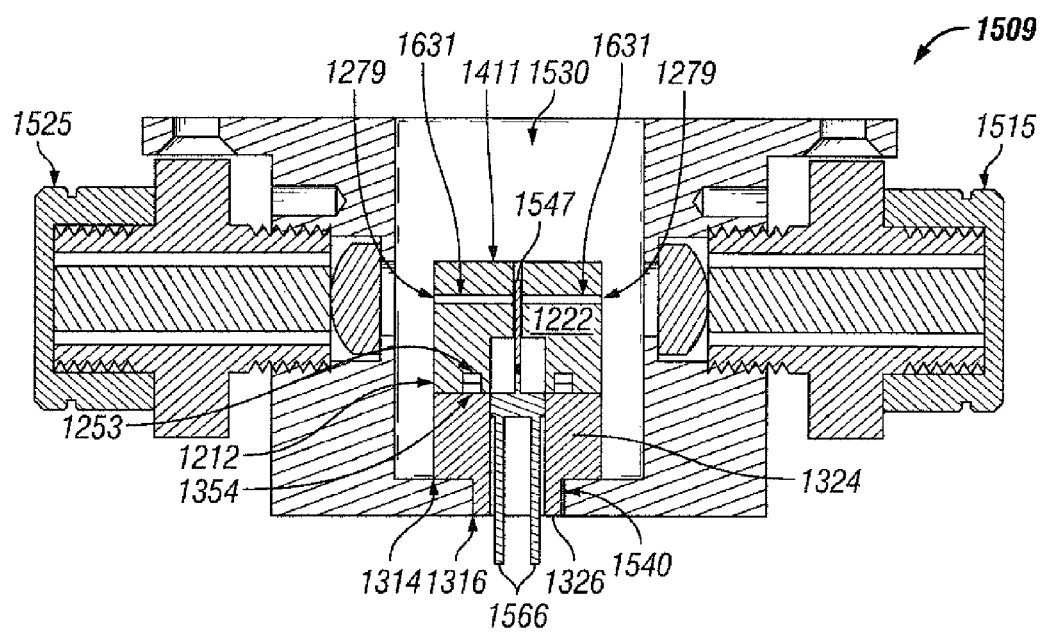

FIGS. 15A and 15B show a subassembly 1503 of a gas sensor that includes the module 1411 of FIGS. 12A-14 and a subassembly 1500, which is substantially similar to the subassembly 100 of FIG. 1, in accordance with certain example embodiments. FIGS. 16A and 16B show detailed views of a portion 1509 of the subassembly 1503 of FIGS. 15A and 15B in accordance with certain example embodiments. Referring to FIGS. 1-16B, the module 1411 of FIG. 14 is disposed, at least in part, within the cavity 1530 of the bottom portion 1502 of the housing 1501. Portion 1316 is coupled to the tuning fork coupling feature 1540 (also called the module coupling feature 1540) of the bottom portion 1502 of the housing 1501. The tuning fork 1545 is coupled to the tuning fork coupling feature 1341 of portion 1314 and the tuning fork coupling feature 1343 of portion 1316 of the module 1411. In addition, the tuning fork 1545 is disposed within the aperture 1241 of portion 1212 of the module 1411.

Further, the micro-resonator coupling features 1279 of portion 1212 are configured in such a way that a micro-resonator 1631 coupled to one of the micro-resonator coupling features 1279 of portion 1212 directs light emitted by the optical device 1525 toward the tines 1547 of the tuning fork 1545. Also, the other micro-resonator coupling feature 1279 of portion 1212 is configured in such a way that another micro-resonator 1631 coupled to the micro-resonator coupling feature 1279 of portion 1212 directs light emitted through the tines 1547 of the tuning fork 1545 toward the optical device 1515. The tines 1547 of the tuning fork 1545 are disposed within the gap 1295 between the distal ends of the micro-resonators (which, in this case, coincides with the distal ends of the micro-resonator coupling features 1279 of portion 1212.

The example modules described herein can have the various coupling features (e.g., tuning fork coupling feature, micro-resonator coupling features) configured in such a way as to optimize the effectiveness of the gas sensor. For example, as described above, the focus of one or more converging lenses of one or more optical devices lies substantially exactly in between the tines of a tuning fork and also at a height (e.g., two-thirds of the height of the tines) relative to the base of the tuning fork. In such a case, optimal optical alignment can be achieved by configuring the various coupling features of the example module in such a way that all elements (e.g., optical device(s), tuning fork) of the gas sensor are aligned along a central axis, and in such a way that the light emitted by an optical device converges at a certain point relative to the tines of a tuning fork.

Example modules described herein can be reconfigured in any of a number of ways so that example modules can be used in any of a number of housings of a gas sensor. The housings of a gas sensor in which example embodiments can be used can have any of a number of configurations (e.g., number of cavities, shape and size of cavity, direction of flow of test gas, direction of flow of tested gas). The example modules can be used in any such housing to couple to and orient one or more micro-resonators within a cavity of the housing in a certain way relative to the tines of a tuning fork. Example embodiments can be used with a gas sensor that has one optical device or multiple optical devices.

Example embodiments provide a number of benefits. Examples of such benefits include, but are not limited to, compliance with one or more applicable standards (e.g., IP65, IEC 60079-28, Zone 1 or Zone 2 compliance), ease in maintaining and replacing components, and more accurate and quicker detection and measurement of impurities in gases. The example modules described herein can reduce/control the effects of flow and/or turbulence of the test gas and/or the tested gas. Example embodiments can also allow for better alignment accuracy within the sensor head cavity so that the test gas can be more accurately tested. The shape, size, and other characteristics of the various components of a gas sensor module, including the example module described herein, can be engineered to achieve optimal flow rate, minimal turbulence, optimal efficiency, and/or any of a number of other performance metric.

Although embodiments described herein are made with reference to example embodiments, it should be appreciated by those skilled in the art that various modifications are well within the scope and spirit of this disclosure. Those skilled in the art will appreciate that the example embodiments described herein are not limited to any specifically discussed application and that the embodiments described herein are illustrative and not restrictive. From the description of the example embodiments, equivalents of the elements shown therein will suggest themselves to those skilled in the art, and ways of constructing other embodiments using the present disclosure will suggest themselves to practitioners of the art. Therefore, the scope of the example embodiments is not limited herein.

What is claimed is:

1. A module for a gas sensor, the module comprising:
a first portion comprising:
 a first body; and
 at least one first micro-resonator coupling feature disposed in and traversing the first body,
 wherein the first body is configured to be disposed within a cavity of a housing of the gas sensor, and
 wherein the at least one first micro-resonator coupling feature is configured to align with at least one optical device of the gas sensor when the first body is disposed within the cavity of the housing of the gas sensor, and
 wherein the at least one first micro-resonator coupling feature is configured to have at least one first micro-resonator disposed therein.

2. The module of claim 1, further comprising:
a second portion comprising:
 a second body; and
 at least one second micro-resonator coupling feature disposed in and traversing the second body,
 wherein the second body is configured to be disposed within the cavity of the housing of the gas sensor, and
 wherein the at least one second micro-resonator coupling feature is configured to align with the at least one optical device of the gas sensor when the second body is disposed within the cavity of the housing of the gas sensor, and
 wherein the at least one second micro-resonator coupling feature is configured to have at least one second micro-resonator disposed therein.

3. The module of claim 2, wherein the at least one first micro-resonator coupling feature and the at least one second micro-resonator coupling feature are substantially aligned with each other.

4. The module of claim 3, wherein the first portion and the second portion are separate pieces.

5. The module of claim 4, further comprising:
a third portion comprising:
 a third body; and
 a tuning fork coupling feature disposed in and traversing the third body at a third location of the third body,
 wherein the tuning fork coupling feature is configured to have a tuning fork disposed therein.

6. The module of claim 5, further comprising:
a fourth portion coupled to the third portion, wherein the fourth portion comprises a housing coupling feature that is configured to couple to a complementary coupling feature of a housing of the gas sensor.

7. The module of claim 6, wherein the third portion is a separate piece from the first portion and the second portion.

8. The module of claim 1, further comprising:
a second portion comprising:
 a second body; and
 a first tuning fork coupling feature disposed in and traversing the second body at a second location of the second body,
 wherein the first tuning fork coupling feature is configured to have a tuning fork disposed therein.

9. The module of claim 8, wherein the first portion and the second portion are separate pieces, wherein the first portion further comprises at least one second portion coupling feature, wherein the second portion further comprises at least one first portion coupling feature, and wherein the at least one first portion coupling feature couples to the at least one second portion coupling feature.

10. The module of claim 9, wherein the first portion further comprises an aperture that traverses through the first body, wherein the aperture is configured to receive a portion of the tuning fork, wherein the aperture is transverse and substantially perpendicular to the at least one first micro-resonator coupling feature, and wherein the aperture is substantially aligned with the first tuning fork coupling feature when the first portion and the second portion are coupled to each other.

11. The module of claim 10, wherein the first portion further comprises a second tuning fork coupling feature adjacent to the aperture, wherein the second tuning fork coupling feature is configured to receive a portion of the tuning fork, wherein the second tuning fork coupling feature is substantially aligned with the first tuning fork coupling feature and the aperture when the first portion and the second portion are coupled to each other.

12. The module of claim 11, further comprising:
a third portion coupled to the third portion, wherein the third portion comprises a housing coupling feature that is configured to couple to a complementary coupling feature of a housing of the gas sensor.

13. A housing for a gas sensor module, the housing comprising:
a first housing portion comprising:
 at least one first wall forming a first cavity;
 a first optical device coupling feature disposed at a first location in the at least one first wall, wherein the first location is adjacent to the first cavity; and
 a module coupling feature disposed at a second location in the at least one first wall, wherein the second location is adjacent to the first cavity; and
a module disposed within the first cavity and coupled to the first housing portion, wherein the module comprises:
 a first portion comprising:
  a first body; and
  at least one first micro-resonator coupling feature disposed in and traversing the first body; and
 a second portion comprising:
  a second body; and
  a housing coupling feature disposed in the second body, wherein the housing coupling feature couples to the module coupling feature of the first housing portion,
 wherein the at least one first micro-resonator coupling feature is aligned with the first optical device coupling feature of the first housing portion,
 wherein the first optical device coupling feature is configured to have a first optical device disposed therein, and
 wherein the at least one first micro-resonator coupling feature is configured to have at least one first micro-resonator disposed therein.

14. The housing of claim 13, wherein the first housing portion further comprises a second optical device coupling feature disposed in a second location in the at least one first wall, wherein the second location is adjacent to the first cavity, wherein the module further comprises a third portion comprising a third body and a second micro-resonator coupling feature disposed in and traversing the third body, wherein the second micro-resonator coupling feature is aligned with the second optical device coupling feature, wherein the second optical device coupling feature is configured to have a second optical device disposed therein, and wherein the second micro-resonator coupling feature is configured to have at least one second micro-resonator disposed therein.

15. The housing of claim 14, wherein the first optical device coupling feature, the at least one first micro-resonator coupling feature, the second optical device coupling feature, and the second micro-resonator coupling feature are substantially aligned with each other.

16. The housing of claim 15, wherein the second portion of the module further comprises a tuning fork coupling feature disposed in and traversing the second body, wherein the tuning fork coupling feature is configured to have a tuning fork disposed therein.

17. The housing of claim 16, wherein the module further comprises a third portion comprising a third body and at least one second micro-resonator coupling feature disposed in and traversing the second body, and wherein the second portion of the module further comprises a tuning fork coupling feature disposed in and traversing the second body, wherein the tuning fork coupling feature is configured to have a tuning fork disposed therein.

18. The housing of claim 13, wherein the first portion of the module further comprises an aperture that traverses through the first body, wherein the aperture is configured to receive a portion of the tuning fork, wherein the aperture is substantially perpendicular to the at least one first micro-resonator coupling feature, and wherein the aperture is substantially aligned with the tuning fork coupling feature when the first portion of the module and the second portion of the module are coupled to each other.

19. The housing of claim 13, further comprising:
a second housing portion comprising:
  at least one second wall forming a second cavity;
  a distribution channel disposed at a third location in the at least one second wall, wherein the third location is adjacent to the second cavity, and wherein the distribution channel is configured to deliver test gas from the second cavity to the first cavity; and
  a receiving channel disposed in a fourth location in the at least one second wall, wherein the fourth location is adjacent to the second cavity, and wherein the receiving channel is configured to remove tested gas from the first cavity to the second cavity.

20. A gas sensor, comprising:
a housing comprising;
  at least one wall forming a cavity;
  at least one optical device coupling feature disposed at a first location in the at least one wall, wherein the first location is adjacent to the cavity; and
  a first tuning fork coupling feature disposed at a second location in the at least one wall, wherein the second location is adjacent to the cavity;
a module disposed within the cavity, wherein the module comprises:
  a body;
  at least one micro-resonator coupling feature disposed in and traversing the body at a second location of the body; and
  a second tuning fork coupling feature disposed in and traversing the body at a third location of the body, wherein the second tuning fork coupling feature is substantially perpendicular to the at least one micro-resonator coupling feature,
at least one optical device coupled to the at least one optical device coupling feature of the housing;
at least one micro-resonator coupled to the at least one micro-resonator coupling feature of the module;
a tuning fork coupled to the first tuning fork coupling feature of the housing and the second tuning fork coupling feature of the module,
wherein the at least one micro-resonator and the at least one optical device are substantially aligned with each other.

* * * * *